(12) United States Patent
Kyle et al.

(10) Patent No.: US 9,907,728 B2
(45) Date of Patent: *Mar. 6, 2018

(54) FLUID MANAGEMENT DEVICES AND METHODS

(71) Applicant: SpineSmith Holdings, LLC, Austin, TX (US)

(72) Inventors: Matthew R. Kyle, Plymouth, MN (US); Kyle W. Swartout, Savage, MN (US)

(73) Assignee: SpineSmith Holdings, LLC, Austin, TX (US)

( * ) Notice: Subject to any disclaimer, the term of this patent is extended or adjusted under 35 U.S.C. 154(b) by 200 days.

This patent is subject to a terminal disclaimer.

(21) Appl. No.: 14/032,469

(22) Filed: Sep. 20, 2013

(65) Prior Publication Data

US 2014/0020788 A1 Jan. 23, 2014

Related U.S. Application Data

(63) Continuation of application No. 13/060,185, filed as application No. PCT/US2009/004788 on Aug. 21, 2009, now Pat. No. 8,551,068.

(60) Provisional application No. 61/189,737, filed on Aug. 22, 2008.

(51) Int. Cl.
| | |
|---|---|
| *A61J 1/20* | (2006.01) |
| *B65B 3/00* | (2006.01) |
| *A61M 39/18* | (2006.01) |
| *A61M 39/16* | (2006.01) |

(52) U.S. Cl.
CPC ............... *A61J 1/20* (2013.01); *A61J 1/2089* (2013.01); *A61J 1/2096* (2013.01); *A61M 39/165* (2013.01); *A61M 39/18* (2013.01); *B65B 3/003* (2013.01); *A61J 1/2058* (2015.05); *A61J 1/2062* (2015.05); *A61M 2205/125* (2013.01); *A61M 2205/586* (2013.01); *A61M 2205/6081* (2013.01)

(58) Field of Classification Search
CPC .................................... A61J 1/20; B65B 3/00
See application file for complete search history.

(56) References Cited

U.S. PATENT DOCUMENTS

| | | | |
|---|---|---|---|
| 3,696,920 A | 10/1972 | Lahay | |
| 4,048,999 A | 9/1977 | Kobel | |
| 4,743,229 A | 5/1988 | Chu | |
| 4,863,454 A | 9/1989 | LaBove | |
| 4,971,271 A | 11/1990 | Sularz | |
| 5,067,948 A * | 11/1991 | Haber ................. | A61M 5/2448 604/192 |
| 5,226,892 A | 7/1993 | Boswell | |

(Continued)

FOREIGN PATENT DOCUMENTS

| | | |
|---|---|---|
| JP | 5-7328 | 2/1993 |
| JP | 11319087 | 11/1999 |

(Continued)

*Primary Examiner* — Tatyana Zalukaeva
*Assistant Examiner* — Sara Sass
(74) *Attorney, Agent, or Firm* — Winstead PC

(57) ABSTRACT

A fluid management system for transferring fluid, the system including a connector component comprising a first end and an opposite second end, a first syringe with a distal end that is removably attachable to the first end of the connector component, and a second syringe with a distal end that is removably attachable to the second end of the connector component.

14 Claims, 26 Drawing Sheets

(56) References Cited

U.S. PATENT DOCUMENTS

| | | | |
|---|---|---|---|
| 5,350,357 | A | 9/1994 | Kamen et al. |
| 5,378,233 | A * | 1/1995 | Haber ................ A61M 5/19 |
| | | | 604/135 |
| 5,669,887 | A * | 9/1997 | Cooper .................. 604/195 |
| 5,707,331 | A | 1/1998 | Wells |
| 6,632,189 | B1 | 10/2003 | Fallen et al. |
| 6,716,187 | B1 | 4/2004 | Jorgensen et al. |
| 7,135,027 | B2 | 11/2006 | Delmotte |
| 7,172,071 | B2 | 2/2007 | Hawkins |
| 7,294,132 | B2 | 11/2007 | Raskin et al. |
| 7,331,462 | B2 | 2/2008 | Steppe |
| 7,364,657 | B2 | 4/2008 | Mandrusov et al. |
| 7,745,106 | B2 * | 6/2010 | Beretta ............. A61L 24/106 |
| | | | 210/515 |
| 8,551,068 | B2 * | 10/2013 | Kyle et al. ................ 604/416 |
| 2002/0169408 | A1 * | 11/2002 | Beretta ......... A61B 17/00491 |
| | | | 604/19 |
| 2004/0071786 | A1 * | 4/2004 | Grippi ............... A61L 24/106 |
| | | | 424/530 |
| 2004/0215129 | A1 | 10/2004 | Edgson et al. |
| 2005/0027240 | A1 * | 2/2005 | Fehr ..................... A61C 5/064 |
| | | | 604/82 |
| 2005/0209555 | A1 * | 9/2005 | Middleton et al. ........... 604/82 |
| 2007/0282297 | A1 | 12/2007 | Knight |

FOREIGN PATENT DOCUMENTS

| | | |
|---|---|---|
| JP | 2001198216 | 7/2001 |
| WO | WO 1999/045851 | 9/1999 |
| WO | WO 2004/108060 | 12/2004 |
| WO | WO 2010/021749 | 2/2010 |

* cited by examiner

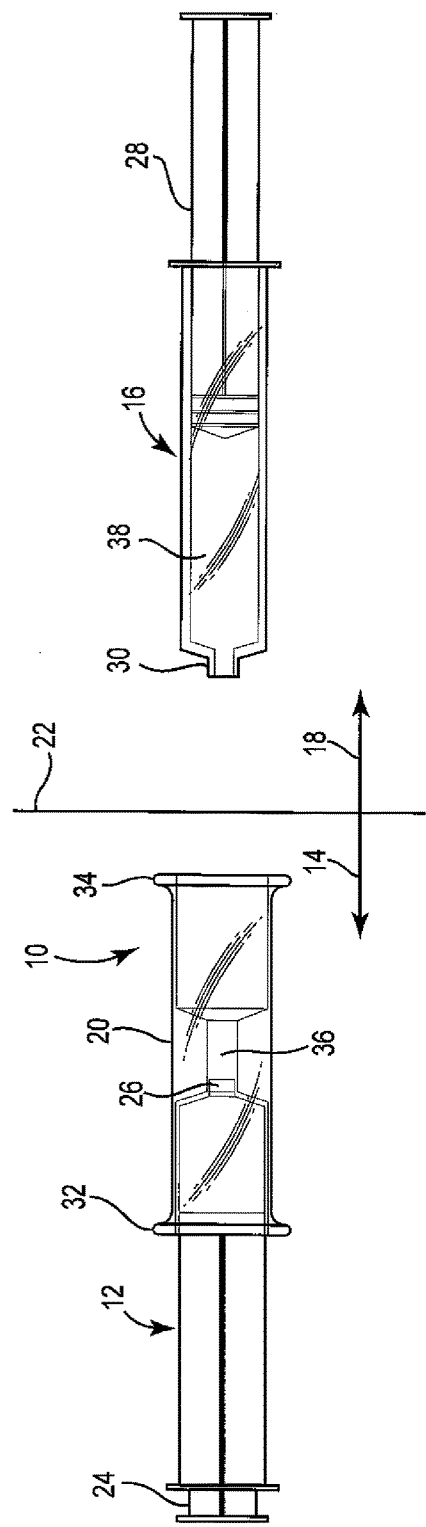
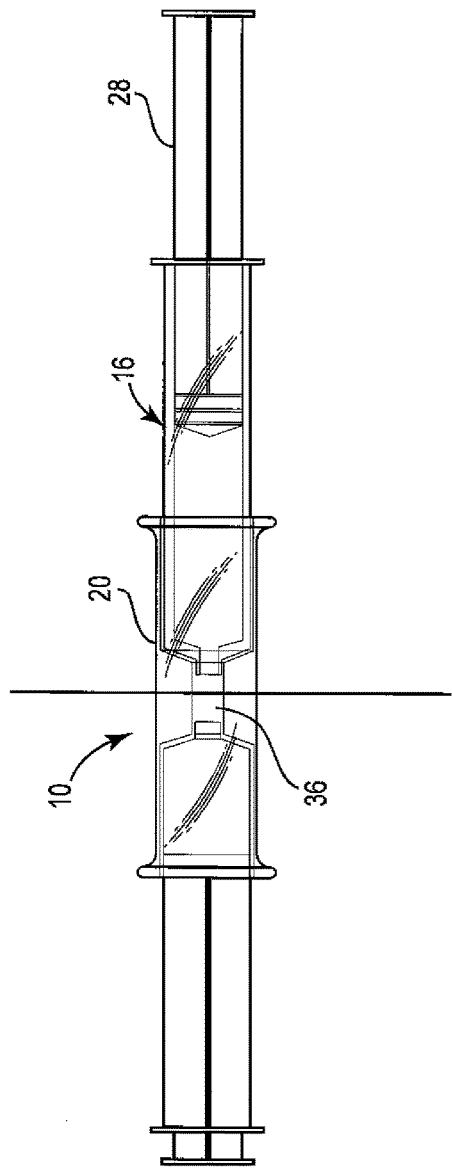
Fig. 1
Fig. 2

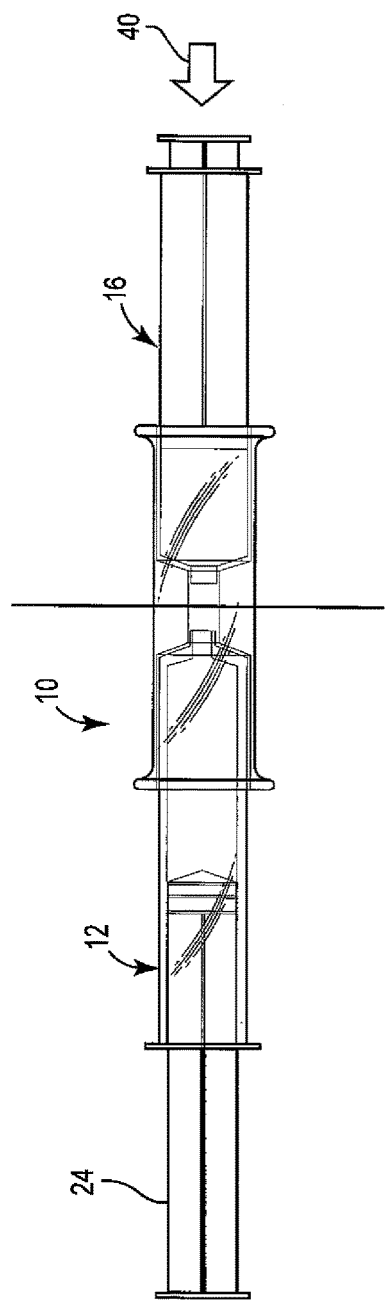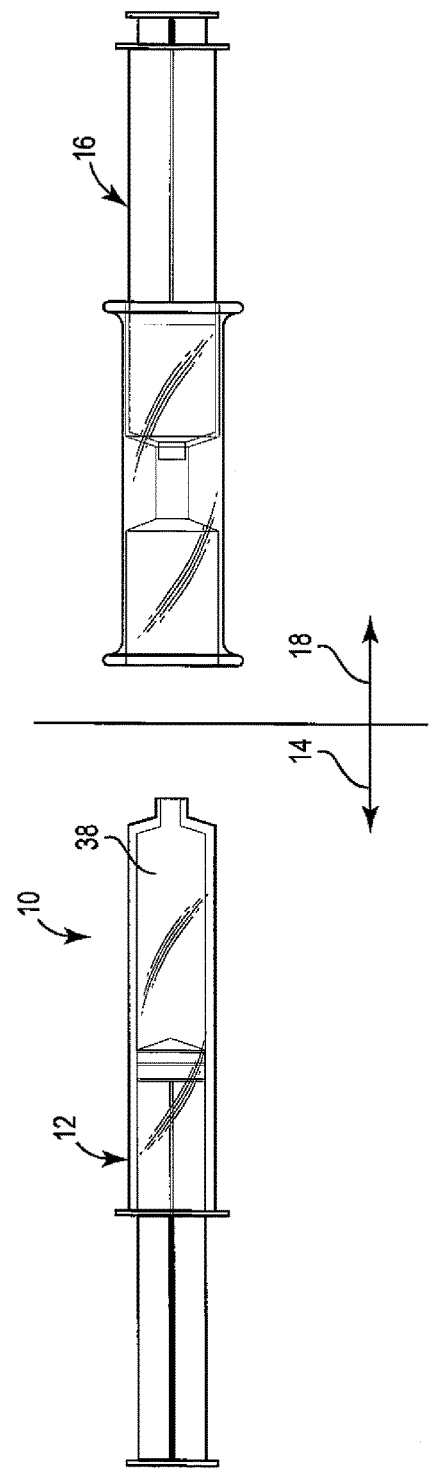
Fig. 3
Fig. 4

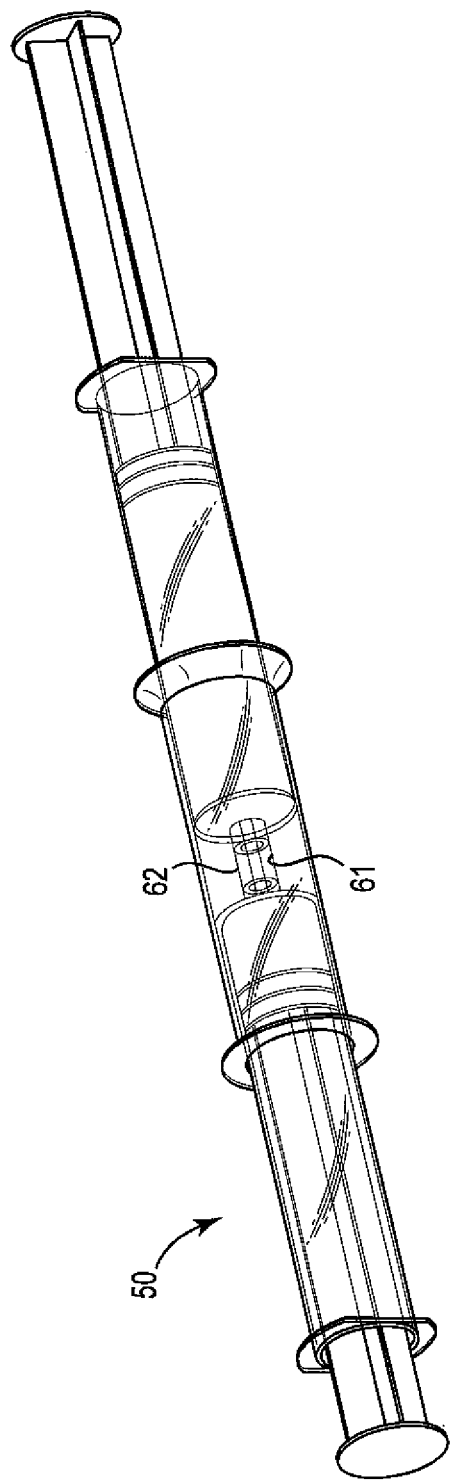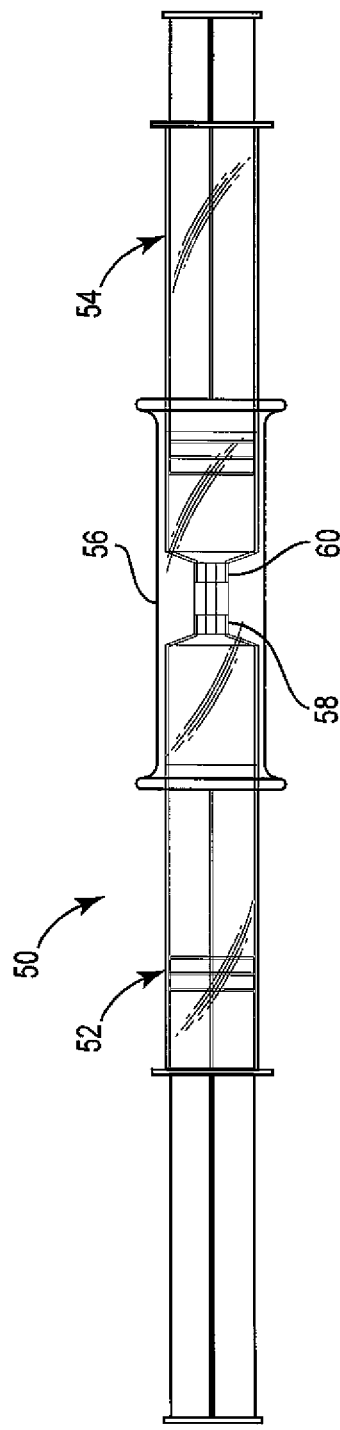
Fig. 5
Fig. 6

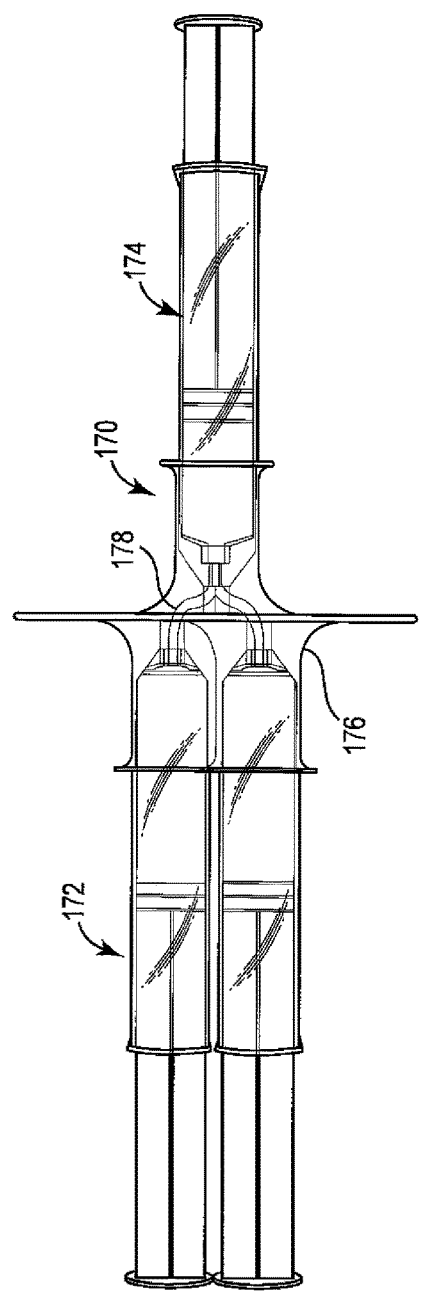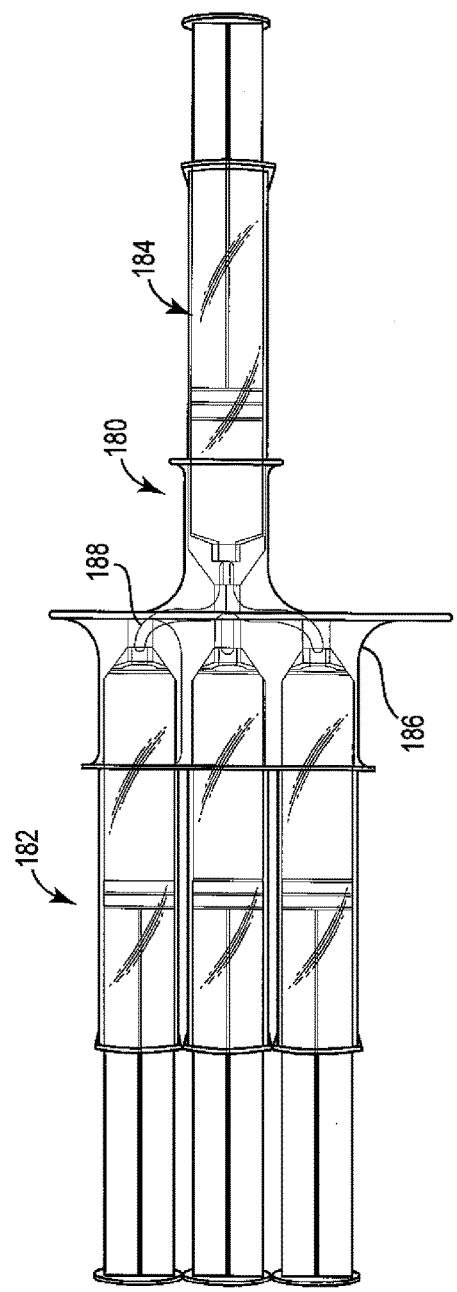

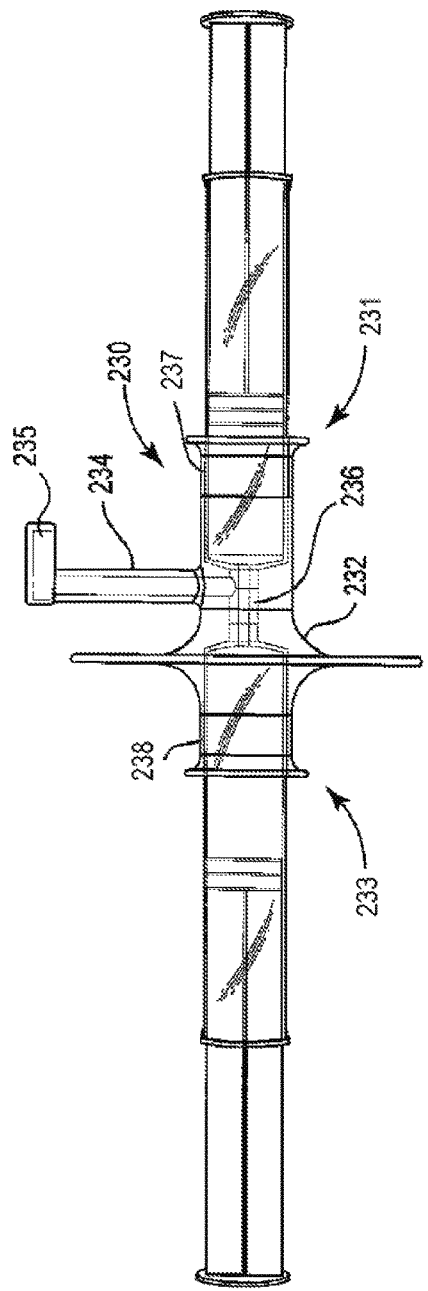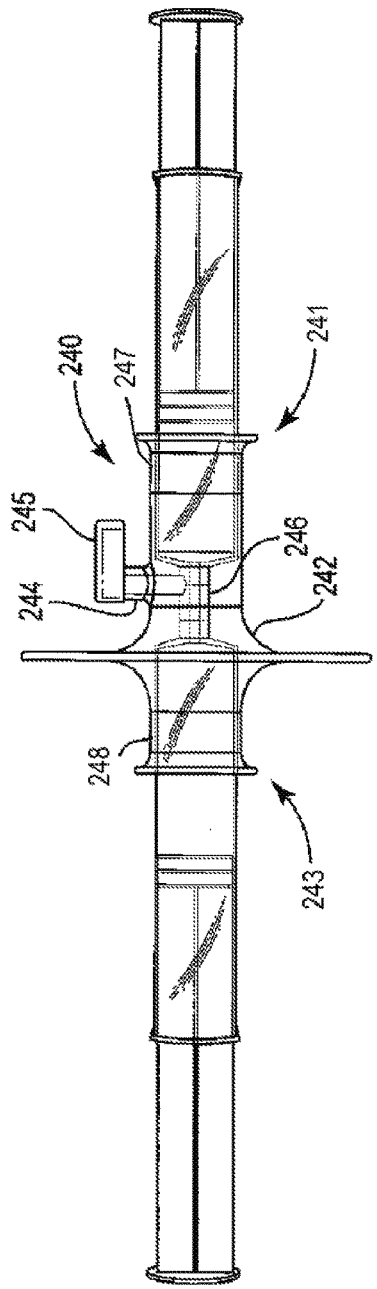

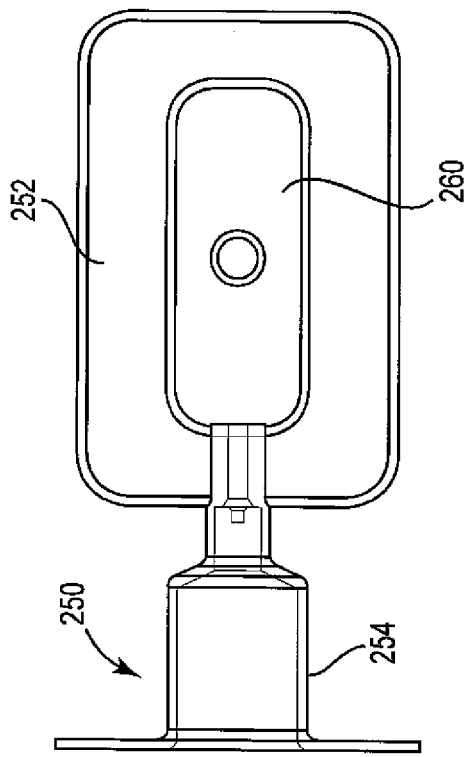
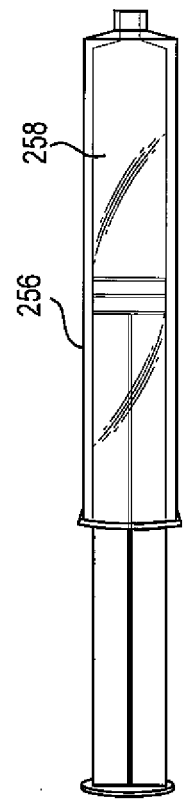
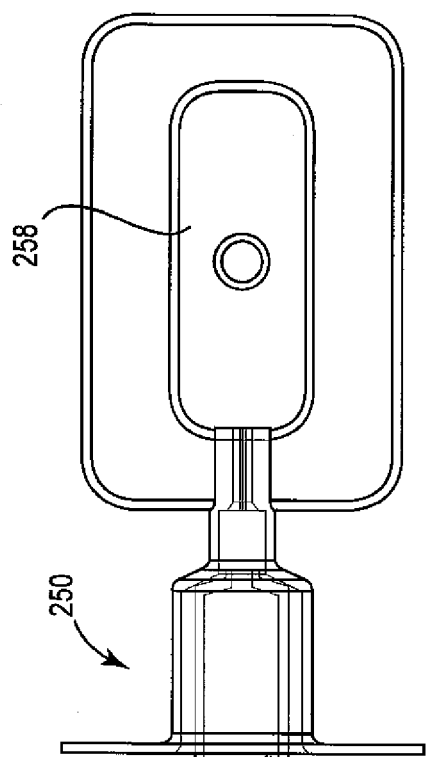
Fig. 25
Fig. 26

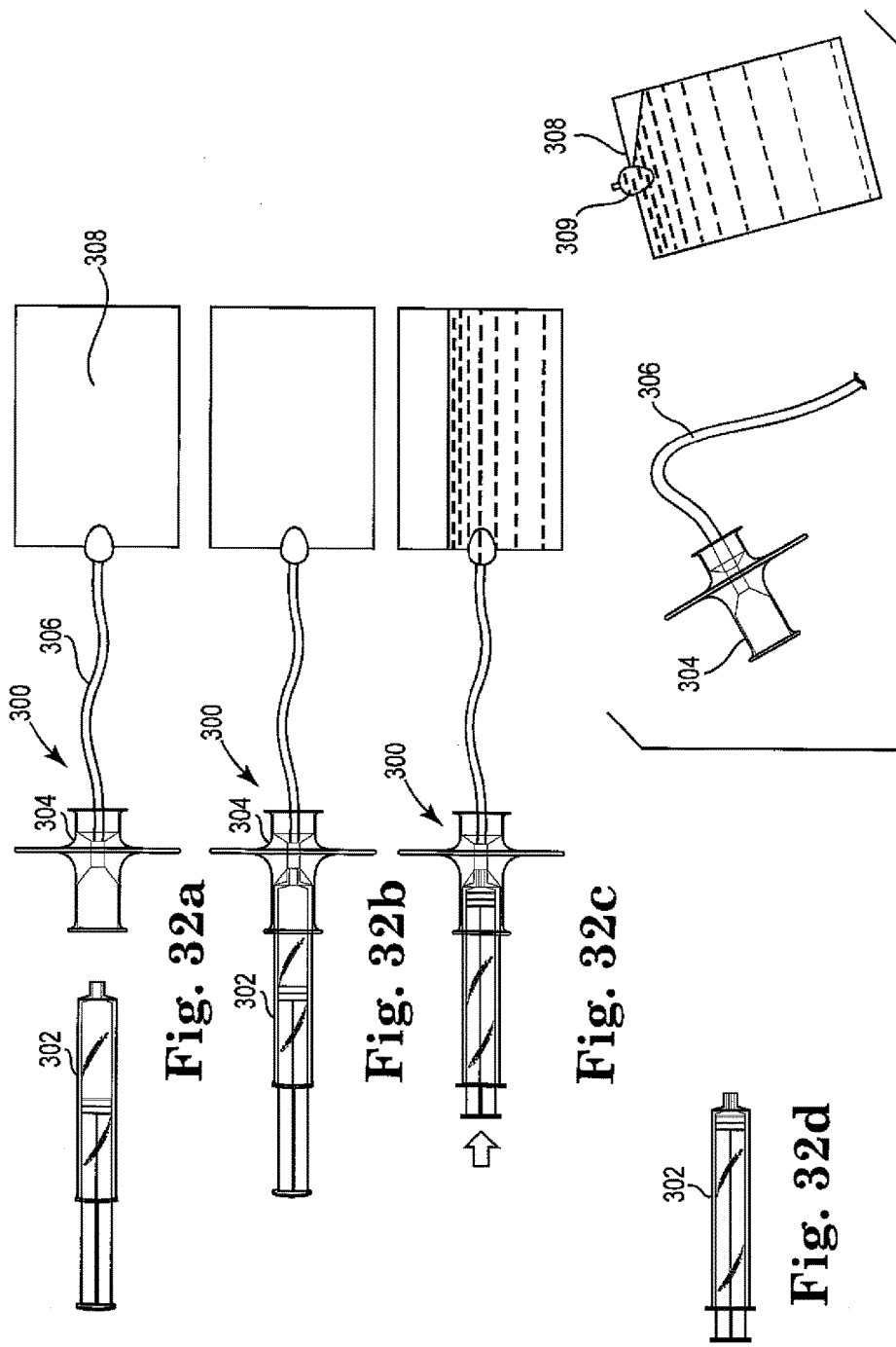

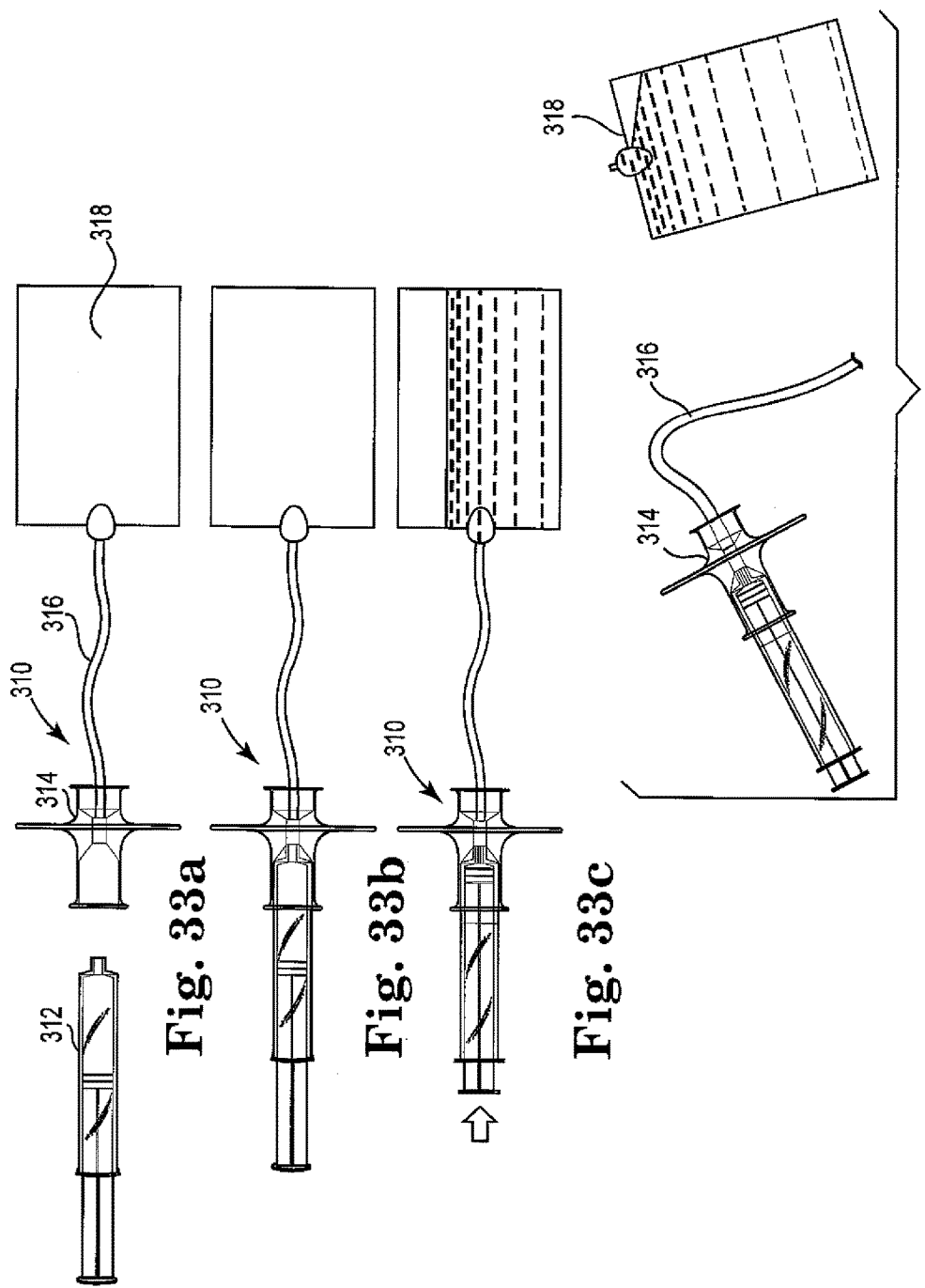

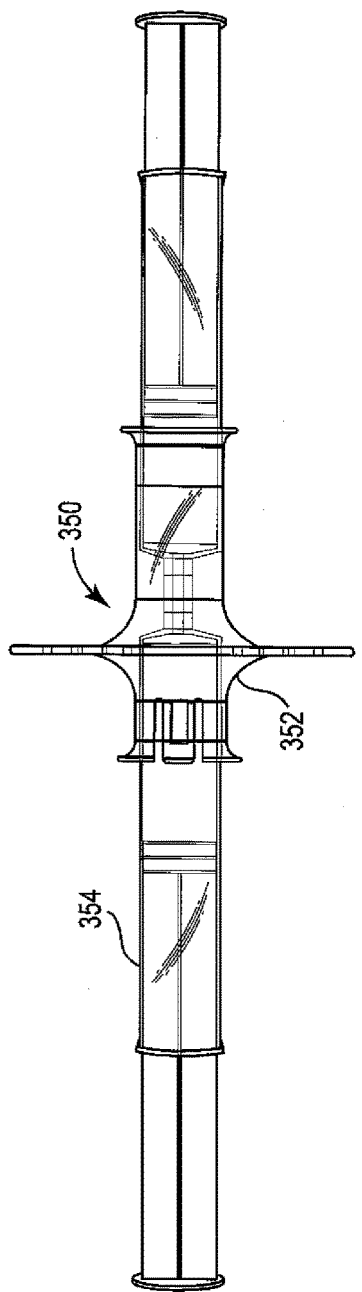
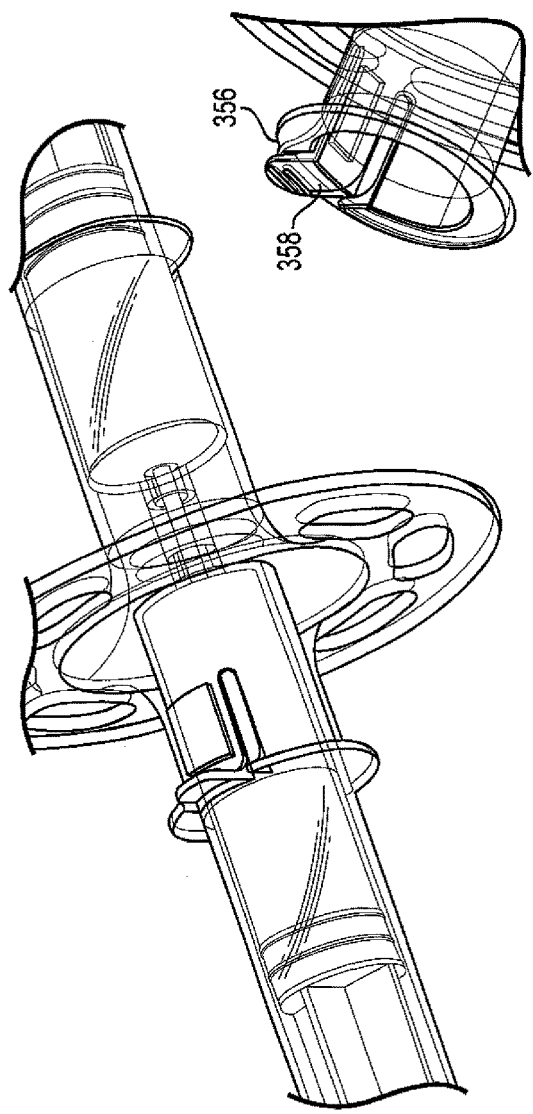
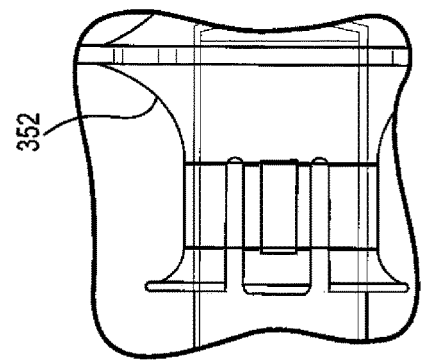
Fig. 36
Fig. 37a
Fig. 37b
Fig. 37c

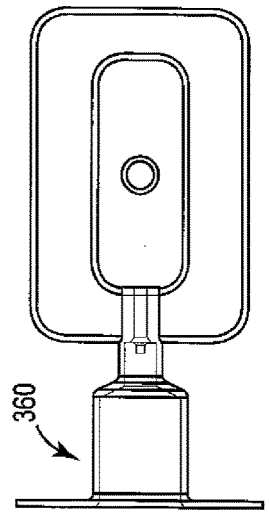
Fig. 38a
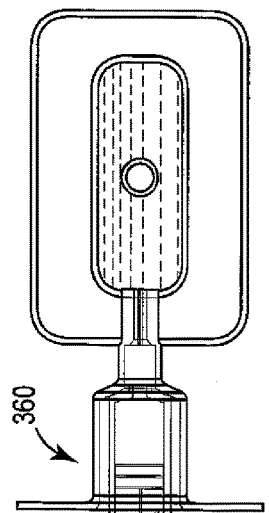
Fig. 38b
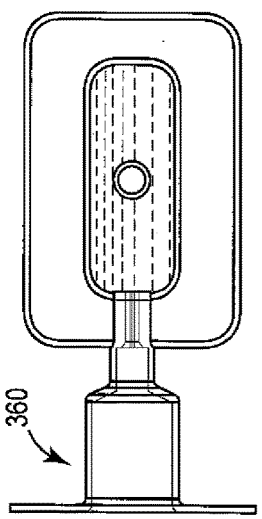
Fig. 38c
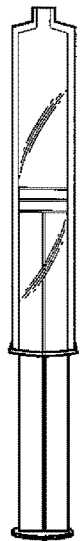

FLUID MANAGEMENT DEVICES AND METHODS

CROSS-REFERENCE TO RELATED APPLICATION

The application is a continuation application of U.S. Nonprovisional application Ser. No. 13/060,185, filed May 24, 2011, and titled "Fluid Management Devices and Methods", which claims benefit from International Application No. PCT/US2009/004788, which was filed on Aug. 21, 2009, which in turn claims priority to U.S. Provisional Application No. 61/189,737, filed Aug. 22, 2008, which applications are incorporated herein by reference in their entireties.

TECHNICAL FIELD

The present invention relates to the management of fluids in medical or laboratory applications, and more particularly relates to devices, methods, and kits for transferring fluids in a controlled environment.

BACKGROUND

A surgical or invasive care suite is typically classified into separate types of areas, which include one or more "sterile" fields and one or more "non-sterile" fields. The sterile and non-sterile fields are typically included in the same physical space (e.g., a single operating room), with an imaginary vertical barrier being the only separation between these areas. In general, the sterile fields include areas where the highest level of sterility is required, which include the patient on which the procedure is being performed, the doctors, surgeons, and other medical personnel participating in the surgical procedure, the instruments and medical equipment required for the surgical procedure, and the entire area that immediately surrounds the sterile equipment and personnel. The sizes of these areas are preferably made to be as small as possible due to the difficulty and costs associated with maintaining sterile environments. For example, a sterile field may comprise only a table holding sterile instruments, along with the space immediately above that object. The non-sterile fields will typically comprise the remainder of the surgical suite that is not included in the sterile field or fields, which can include all equipment and personnel that are needed for the surgery but that need not be maintained in a completely sterile condition. However, it is typical to prepare or configure equipment, fluid, instruments, or other items in the non-sterile areas for transfer into the sterile area to be used in the surgical procedure. Several methods and devices have been created for such a transfer of equipment and materials so that the sterility plane is not broken; however, this can be difficult to accomplish, particularly when the item being transferred is a volume of fluid.

In current applications, a fluid may be prepared in a non-sterile environment and subsequently transferred to a sterile environment in such a way that the fluid does not become contaminated. One method of performing such a fluid transfer is to first provide the fluid to a syringe by placing a sterile syringe tip into the fluid and drawing it into the barrel of the syringe, such as by withdrawing a plunger of the syringe relative to the syringe barrel. This fluid is then transferred to the sterile field by positioning the syringe so that it crosses the plane between the sterile and non-sterile fields, and then discharging the fluid into an open, sterile container (e.g., a sterile bowl or similar container) that is preferably immediately adjacent to the boundary between the fields. The fluid is then available for use in the sterile area of the surgical suite. Although this method can be satisfactory in some circumstances, there is a risk of fluids being spilled during or after the process of transferring fluid to an open container and there is also a risk that the non-sterile syringe will come in contact with and thereby contaminate the sterile bowl or other items in the sterile field. In addition, it can often be difficult to remove all of the fluid from the open container in cases where fluid is being removed using an instrument such as syringe. This can thereby result in fluid being left behind in the container, which will often be discarded since it cannot be saved or reused. In some cases, such fluid loss can be acceptable, but in cases where the fluid is very expensive and/or rare, for example, the loss of even a tiny amount of fluid can be unacceptable. Similarly, fluids containing cellular or protein therapies, and the like, may become activated or otherwise caused to undergo unwanted changes. There is therefore a need for a fluid management system that minimizes the risks and costs described above while transferring fluid between a non-sterile environment and a sterile environment and/or between other types of environments.

SUMMARY

In one aspect of the invention, a device or system is provided for transferring fluid from a non-sterile environment to a sterile environment without contacting and possibly contaminating the fluid. The device or system comprises a syringe assembly that includes a first syringe, a second syringe, and a connector component or docking station. The connector component has a first end that is attachable to a first syringe in a sterile environment when the first syringe does not contain fluid. The second syringe, which is in a non-sterile environment, is used to pull a quantity of fluid from a fluid supply location into its internal barrel and will be used for transferring this fluid to the first syringe. The first and second syringes are then brought together at the barrier between the sterile and non-sterile environments, with at least a portion of the connector component (with the attached first syringe) being positioned in the non-sterile environment. The second syringe is then inserted into, or otherwise connected to, a second end of the connector component. The second syringe is then activated to eject the fluid that is within its internal barrel and transfer this fluid into the first syringe through the internal area of the connector component.

The connector component of the device or system described above can be provided with a gripping surface that can be grasped by the operator who is holding the second syringe (i.e., the syringe that is in the non-sterile environment). In this way, after the fluid has been transferred to the sterile syringe, the operator in the non-sterile environment can instruct the operator in the sterile environment to disconnect the first syringe (which is now holding the sterile fluid) from the connector component. This may be accomplished by simply pulling the first syringe directly out of the connector component, or through some other method of disconnecting the components from each other. In any case, the operator in the non-sterile environment will then be holding the second syringe with the attached connector component. During this entire procedure, the operators in both the sterile and non-sterile environments do not contact the fluid and fluid pathway, although the connector component can be handled at some point by operators in either or both environments.

In at least one aspect of the invention, the connector component generally is configured as a tube having at least one port on each side. The tube includes at least a portion that can be grasped by an operator and may include features or components that are molded, integrated, or otherwise attached to the outer surface of the tube. These features can provide for a surface that makes it difficult for the component to slip from an operator's hand, particularly during and after the fluid transfer operation.

In another aspect of the invention, one or both ends of the connector component include more than one port. These multiple ports can promote a mixing and/or agitation/activation function for combining two or more fluids during the fluid transfer process. Additional fluid mixing can be facilitated by including ribs, nubs, or other extensions within the fluid pathway between the syringes. The number, size, positioning, orientation, etc. of these extensions can be specifically designed or selected to provide a desired amount of fluid mixing. The specific desired mixing forces necessary for particularly components will be a factor in determining the characteristics for the mixing elements.

The fluid management systems of the invention may further be provided with filters in one or more locations within the fluid pathway and or nanofibers that are designed to pull out or bind specific components (e.g., certain types or sizes of particles, cells, and/or proteins). The filters may comprise materials capable of acting as a separation medium, a filtration medium, or a growth matrix or surface, for example. In other embodiments, the filters may comprise a network of one or more of the following: nanofibers; a nanofibrillar structure; glass, silicon, or plastic comprising an etched or micropatterned surface; glass, silicon, or plastic comprising macropores or nanopores; or a polymer scaffold. In certain embodiments, the filters may comprise a filter membrane with multiple longitudinally oriented stranded filter lumens.

The fluid management systems of the invention may also include luer ports that are provided in different locations along one or more of the syringes and/or connector components so that additional fluids or substances can be added to and/or mixed with a fluid during its transfer. The system can further include one or more adaptors along the tube line for ease of handling. The fluid pathway tube may additionally include synthetic graft, allograft, xenograft, and the like, which may be provided within a syringe that includes these or different materials to which fluid is added.

Although many of the aspects of the invention are described herein for transfer of a fluid from a non-sterile environment to a sterile environment, it is understood that the same or similar principles, methods and devices can also be used for transferring fluid from a sterile environment to a non-sterile environment, or for transfer of fluids between other similar or different environments. In addition, several aspects of the invention described and shown herein are directed to fluid transfer between syringes; however, it is understood that the same or similar principles, methods and devices can be used with other devices that can contain fluids such as bags, boxes, vials and the like, where fluid can be transferred between similar or different types of fluid containers through a connector component that is attachable to and detachable from both fluid containers.

BRIEF DESCRIPTION OF THE DRAWINGS

The present invention will be further explained with reference to the appended Figures, wherein like structure is referred to by like numerals throughout the several views, and wherein:

FIGS. 1-4 are side views of a fluid management system of the invention and illustrating exemplary sequential steps in a fluid transfer process;

FIGS. 5 and 6 are perspective and side views, respectively, of a fluid management system of the invention;

FIG. 19 is a side view of a fluid management system including two syringes on one side of a connector component and one syringe on another side of the connector component;

FIG. 20 is a side view of a fluid management system including a connector component for attachment of three syringes on one side and one syringe on another side;

FIGS. 23 and 24 are side views of fluid management systems including a Luer valve stick extending from a connector component;

FIGS. 25 and 26 are side views of a fluid management system of the invention and illustrating sequential steps in a fluid transfer process;

FIGS. 32a-32e are side views of a fluid management system of the invention illustrating sequential steps in a fluid transfer process form transferring fluid from a syringe to a bag;

FIGS. 33a-33d are side views of a fluid management system of the invention illustrating sequential steps in a fluid transfer process for transferring fluid from a syringe to a bag;

FIG. 36 is a side view of a fluid management system including a connector component having locking mechanism;

FIGS. 37a-37c are enlarged perspective and side views of a portion of the fluid management system of FIG. 36 and including a locking mechanism;

FIGS. 38a-38c are side views of fluid management systems of the invention illustrating sequential steps in fluid transfer processes including a fluid-receiving container;

DETAILED DESCRIPTION

Figure 7:
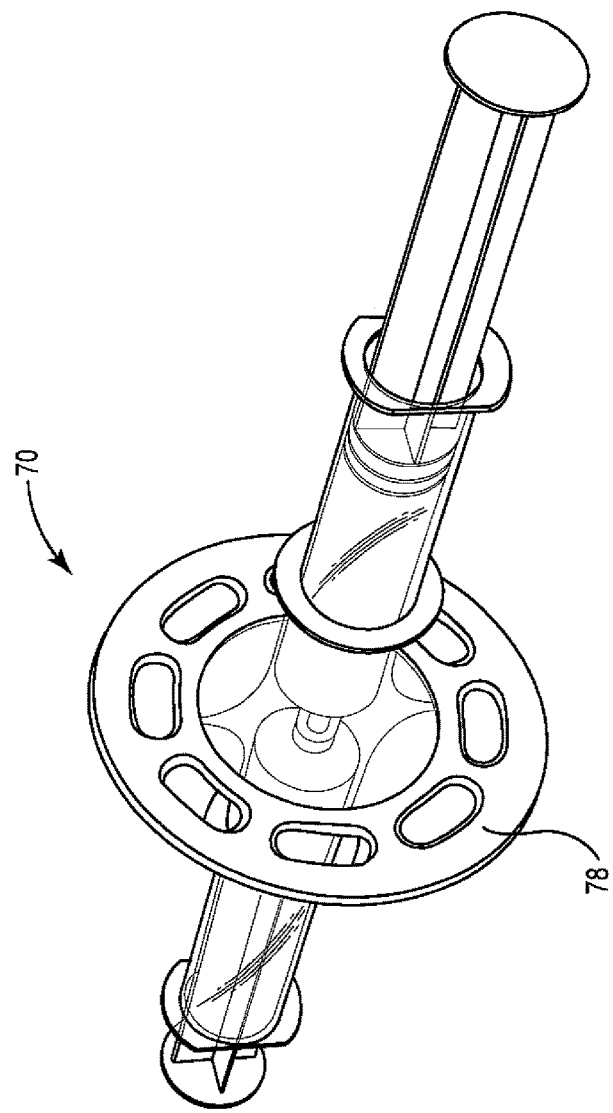
FIGS. 7 and 8 are perspective and side views, respectively, of a fluid management system of the invention that includes a sterile field boundary indicator component.

Referring now to the Figures, wherein the components are labeled with like numerals throughout the several Figures, and initially to FIGS. 1-4, multiple exemplary sequential steps used for one exemplary configuration of a fluid management system 10 and method of the invention are illustrated. In general, the process step using system 10 shown in FIG. 1 includes a first syringe 12 that is positioned entirely within a sterile environment (indicated by arrow 14 as the area to the left of a schematic barrier line 22), a second syringe 16 that is positioned entirely within a non-sterile environment (indicated by arrow 18 as the area to the right of schematic barrier line 22), and a connector component or docking station 20 attached to the distal end of the first syringe 12. The first syringe 12 includes a plunger 24 at its proximal end and a tip element 26 at its distal end. The second syringe 16 similarly includes a plunger 28 at its proximal end and a tip element 30 at its distal end. The first and second syringes 12, 16 may be identical to each other, or the syringes may be structured at least somewhat differently from each other.

The connector component 20 is a generally tubular structure that includes an outer surface that is cylindrical and an inner area that is configured for mating with the distal ends of the first and second syringes 12, 16. In particular, the connector component 20 includes a first end 32 that can be engaged with the first syringe 12 and a second end 34 that can be engaged with the second syringe 16. The inner area at the first end 32 of the connector component 20 is an area or opening that is designed to accept the distal end of the first syringe 12, preferably with a slideable and frictional fit between the components. Similarly, the inner area at the second end 34 of the connector component 20 is an area or opening designed to accept the distal end of the second syringe 16, preferably with a slideable and frictional fit between the components. The inner area of the connector component 20 is further provided with a channel 36 for fluid communication between the inner areas of its first and second ends 32, 34.

Referring again to the process step illustrated in FIG. 1, the first syringe 12 is inserted into the first end 32 of the connector component 20 with its plunger 24 fully inserted into the barrel of the first syringe 12. That is, the first syringe 12 preferably does not contain any fluid at this point, although it is possible that some substance, such as another fluid or material, has been provided within its barrel. This would require an expression port or would require that the plunger 24 be retracted at least somewhat from the syringe barrel. In either case, both the first syringe 12 and the connector component 20 are positioned within the sterile environment 14. At this stage, the second syringe 16 is provided with a volume of sterile fluid 38 within its internal barrel, which may have been transferred to this syringe 16 by positioning the tip element 26 in fluid and withdrawing the plunger 28 from the barrel until a desired amount of fluid was withdrawn. At this point, the second syringe is positioned entirely within the non-sterile environment 18. The barrier or boundary 22 between the sterile and non-sterile environments 14, 18 is shown in the Figures as a vertical line, although it is understood that this boundary 22 can be a generally vertical plane that extends from the edge of a sterile surface (e.g., a draped table or patient bed).

The first syringe 12 and its attached connector component 20 are then brought to the boundary 22 between the sterile environment 14 and non-sterile environment 18 until at least a portion of the connector component 20 crosses through or over the boundary 22, as is illustrated in FIG. 2. The second syringe 16 is then inserted into the second end 34 of the connector component 20 until it is nested within the inner area of the connector component 20. At this point, the tip elements 26, 30 of the first and second syringes 12, 16, respectively, are shown as at least partially extending into the channel 36 within the connector component 20. In order to avoid contamination of the fluid 38 and/or syringes 12, 16 or other instruments, the tip elements 26, 30 are designed so that they do not contact each other within the connector component 20. Rather, the channel 36 can be at least slightly longer than the combined lengths of the tip elements 26, 30 when they are fully inserted into the channel 36, thereby providing a gap or space between the tip elements 26, 30. Alternatively, the connector component 20 can have an additional or alternative structure or device that prevents the tip elements 26, 30 from contacting each other.

When it is desired to transfer the fluid 38 from the second syringe 16 to the first syringe 12, the plunger 28 of the second syringe 16 is activated or pushed toward the distal end of the syringe (as illustrated by the arrow 40 in FIG. 3), thereby pushing the fluid 38 from its internal barrel and toward the first syringe 12. The sterile fluid 38 will move toward the distal end of the second syringe 16, through the tip element 30 of the second syringe 16, and into the channel 36 of the connector component 20. The plunger 24 of the first syringe 12 can simultaneously be pulled outward from the barrel of the first syringe 12, thereby drawing fluid 38 from the channel 36 of the connector component 20 into the barrel of the first syringe 12 through the tip element 26. It is also contemplated that the pressure of the fluid 38 being pushed through the channel 36 of the connector component 20 would be sufficient to move the plunger 24 of the first syringe 12 proximally relative to its barrel. After the desired amount of sterile fluid 38 is transferred to the first syringe 12, the first syringe 12 can be disconnected from the connector component 20, as is illustrated in FIG. 4. As shown, the connector component 20 and attached second syringe 16 will then remain in the non-sterile environment 18, while the first syringe 12, with sterile fluid 38 contained within its barrel, will be available for use within the sterile environment 14.

As discussed herein, a fluid may be any flowable material that is generally transferable via pressurization between or among chambers, including all components constituting or contained in the fluid. One such exemplary fluid is blood, which contains multiple sub-components such as cells and proteins. In this example, blood, and all of is sub-components would be collectively referred to as a fluid.

FIGS. 5 and 6 illustrate a fluid management system 50 similar to that described above relative to FIGS. 1-4, where several of the components are again shown to be transparent for illustrative purposes. It is noted that the actual components of the systems of the invention can be opaque, although it will be advantageous in some applications for the components to be translucent or transparent in order provide at least some visibility of the fluid transfer process. It is further noted that although many of the embodiments described herein specifically refer to fluid transfer from a non-sterile to a sterile environment, the same concepts, methods, and devices can be used to transfer fluid from a sterile to a non-sterile environment, and/or to transfer fluid within a single field (e.g., within a sterile field, non-sterile field, or the like). Additionally, the concepts, methods, and devices of the invention can be used to transfer fluids between other types of environments or fields.

With regard to FIGS. 5 and 6, the fluid management system 50 includes a first syringe 52 and a second syringe 54. The system 50 may be positioned so that the first and second syringes 52, 54 are in sterile and non-sterile fields, respectively, with the second syringe 54 initially containing the sterile fluid that is to be transferred to the first syringe 52. In this embodiment, FIG. 5 illustrates the first syringe 52 as having a first volume of the sterile fluid within its barrel, and FIG. 6 shows the first syringe 52 with a greater volume of the sterile fluid having been transferred to its barrel via a connector component 56. As with the embodiment of FIGS. 1-4, the first and second syringes 52, 54 are inserted into opposite ends of the connector component 56 until their respective tip elements 58, 60 are positioned within a channel 62 in the internal area of the connector component 56.

With respect to the embodiments of the invention, a channel provided within the internal area of the connector component can include walls or surfaces that define the outer boundaries of the channel. These walls or surfaces can further include a coating to modify the surface properties of the channel to improve fluid flow and/or the ability to handle cellular material. In the embodiment of FIG. 5, for example, a coating 61 is placed on at least a portion of the interior walls of the channel 62.

With respect to the embodiments of the invention, the central area of the channel or fluid transfer area within a connector component can further include at least one selection element or material. This material can be provided as only a small portion of the channel, or may comprise the entire channel. The selection material may be provided with a number of capabilities such as a separation medium (e.g., affinity columns, packed bed matrices and beads, and/or nanofiber networks), a filtration medium, or a growth matrix or surface (e.g., nanofiber networks). One or more ligands can also be attached to a filter element, which can be selected to bind one or more particular growth factors, differentiation factors, chemotactic factors and/or adhesion molecules. The ligands can be immobilized or coupled directly to a solid support material by formation of covalent chemical bonds between particular functional groups on the ligand and reactive groups on the support. The filtration element or material can comprise affinity or chromatography beads or particles that can be, for example, glass, alginate, polymeric or magnetic. These beads or particles are significantly smaller in size than affinity matrices or columns and are therefore particularly useful for microscale biological manipulations.

In cases where the selection material comprises a packed bed matrix or column, the selection material can include a bed of granular material (e.g., sand, wood cellulose, or the like) that retains solid particles that pass through it while allowing fluids to flow freely. In cases where the selection material comprises a nanofiber network, the selection material can include one or more nanofibers, a nanofibrillar structure, or glass, silicon, or plastic surfaces comprising an etched or micropatterned surface, macropores, or nanopores. In yet another alternative, the selection element or material can comprise multiple longitudinally oriented stranded filter lumens through which the filtrate or retentate can move longitudinally.

The connector components of the devices and systems described herein preferably include at least a portion that can be grasped by an operator and may include features or components that are molded, integrated, or otherwise attached to the outer surface of the tube, such as to provide anti-slip gripping surfaces. These features can provide a surface that makes it difficult for the component to slip from an operator's hand, particularly during and after the fluid transfer operation. In particular, the connector components of the devices or systems described herein are preferably provided with a gripping surface that can be grasped by the operator who is holding the second syringe (i.e., the syringe that is in the non-sterile environment) throughout the fluid transfer process. In this way, after the fluid has been transferred to the sterile syringe, the operator in the non-sterile environment can instruct the operator in the sterile environment to disconnect the first syringe (which is now holding the sterile fluid) from the connector component. This may be accomplished by simply pulling the first syringe directly out of the connector component if the connection is through a frictional fit, or through some other method of disconnecting the components from each other if the components were initially connected in some other way. In any case, the operator in the non-sterile environment will then be holding the second syringe within the attached connector component. During this entire procedure, the operators in both the sterile and non-sterile environments do not contact the fluid pathway or any of the fluids contained therein.

Figure 8:
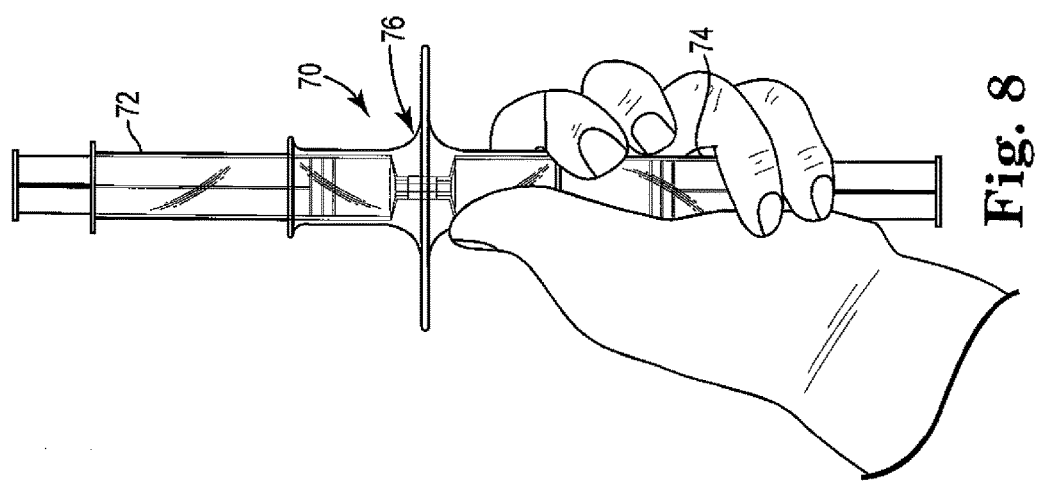

FIGS. 7 and 8 illustrate another aspect of a fluid management system 70 of the invention, which also generally includes first and second syringes 72, 74 that are attachable to a central connector component 76. The connector component 76 of this embodiment is further provided with a sterile field boundary indicator 78, which in this case is illustrated as a slotted disk that extends from the outer surface of the connector component 76. This boundary indicator 78 provides an operator with guidance on where to locate the system 70 during the fluid transfer process in order to keep the sterile and non-sterile components within their respective environments. Thus, the illustrated shape and size of the boundary indicator can be somewhat or considerably different from that shown, where any configuration of the indicator 78 that provides this function to the operators is contemplated by the invention. This boundary indicator can optionally have one or more visual markers on one or both sides to designate which direction the connector component should be oriented, such as color-coding, indicia, or the like. In one embodiment, the connector component includes a ring at one of its ends that also includes a visual marker that corresponds to the visual marker on the sterile field boundary indicator. For example, one side of the boundary indicator can be yellow and a ring or other portion of the connector component and/or syringe can also be yellow to provide the operators with visual assurance of the proper placement of the components of the system.

Figure 10:
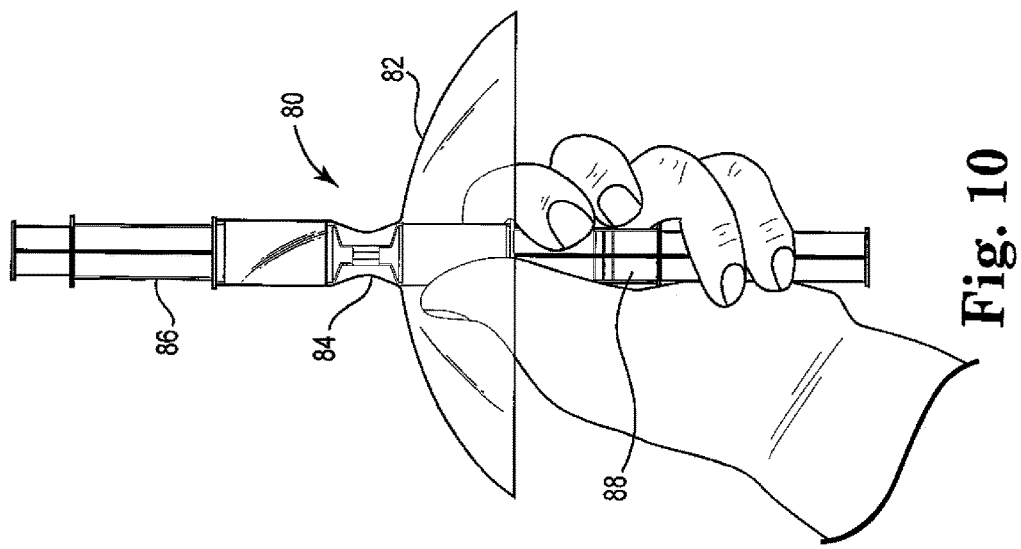
FIGS. 9 and 10 are perspective and side views, respectively, of a fluid management system of the invention that includes a sterile field boundary indicator component.
Figure 9:
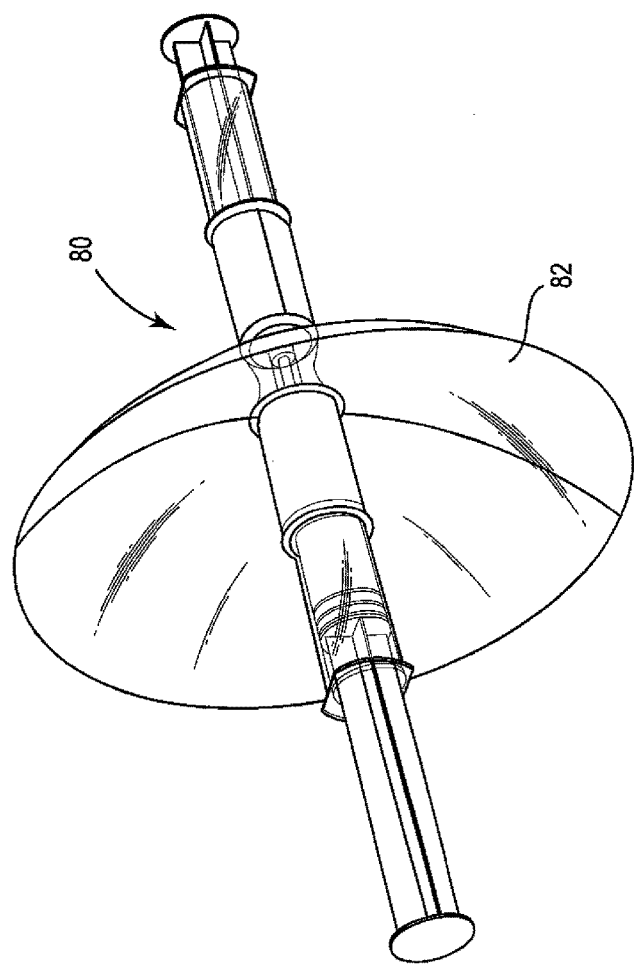

Another embodiment of a fluid management system 80 of the invention having a sterile field boundary indicator 82 is illustrated in FIGS. 9 and 10. This boundary indicator is provided as a curved shield that extends from an outer surface of a connector component 84 of the system. The shield 82 further provides protection for the operator's hand by preventing inadvertent contamination that could be caused by contact between the hands of the operators or other items in the sterile and non-sterile environments. This boundary also provides operators with protection against needle sticks and residual bio fluid or material leakage. Again, this embodiment may be provided with color-coding or other visual indicia on at least a portion of the connector component 84 (e.g., the boundary indicator) to provide guidance to the operators for proper orientation of the system. One or both syringes 86, 88 of this system can be provided with a portion that is color-coded to coordinate with color-coding on the connector component 84 in order to assist the operators in achieving the proper orientation of the components within the system.

Figure 11:
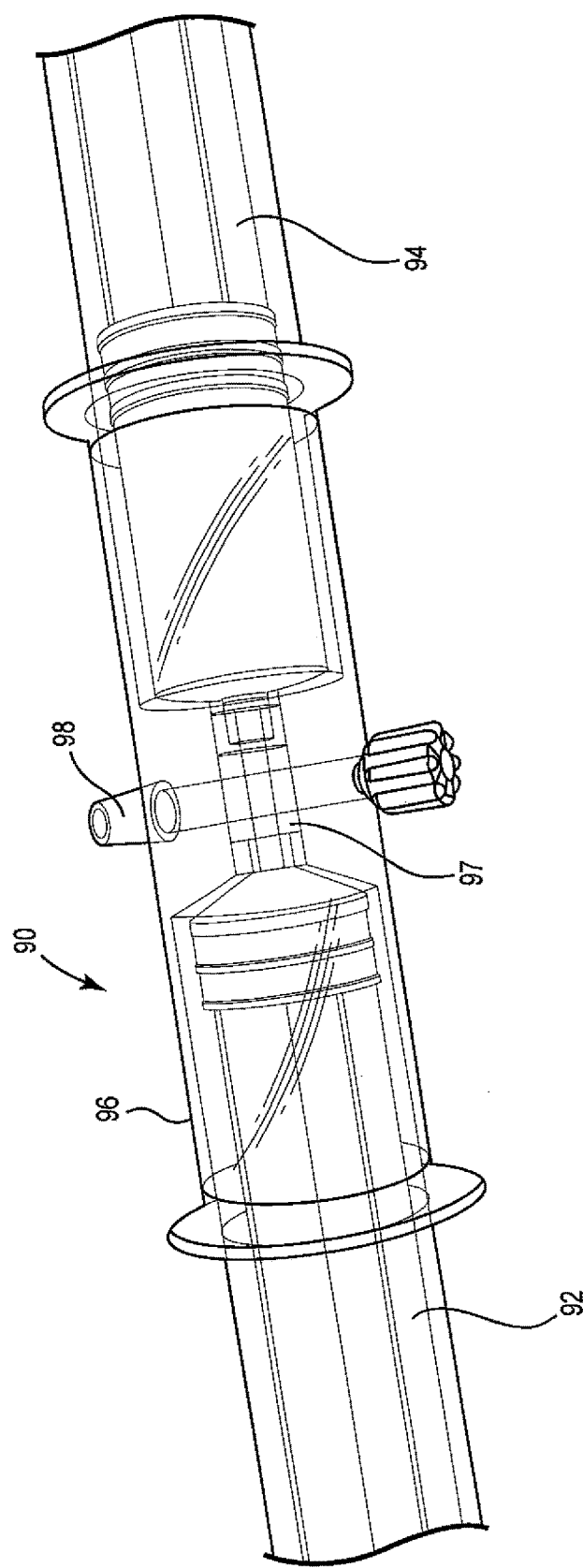
FIG. 11 is a perspective view of a portion of a fluid management system of the invention that includes luer ports that provide a location for the addition of components to the system during fluid transfer.

FIG. 11 illustrates a portion of a fluid management system 90 that includes a first syringe 92 and a second syringe 94, which are each attached to a central connector component 96. The connector component 96 comprises at least one luer port 98 that allows an operator to add materials, such as fluids, to the system 90. Such a transfer of materials to the system 90 can be performed before, during, and/or after the fluid transfer process is completed. As shown, the luer port 98 is in communication with a channel 97 within the connector component 96 of the system, which is the area through which the fluid will flow as it is moved into a sterile syringe. Thus, one or more luer ports 98 can provide a mixing function for combining two or more fluids during the fluid transfer process. Each luer port 98 can optionally include a metering function to provide for the addition of components at a certain ratio or concentration to achieve a final product having certain properties. Luer port 98 can additionally be used to pressurize the channel 97.

Figure 12:
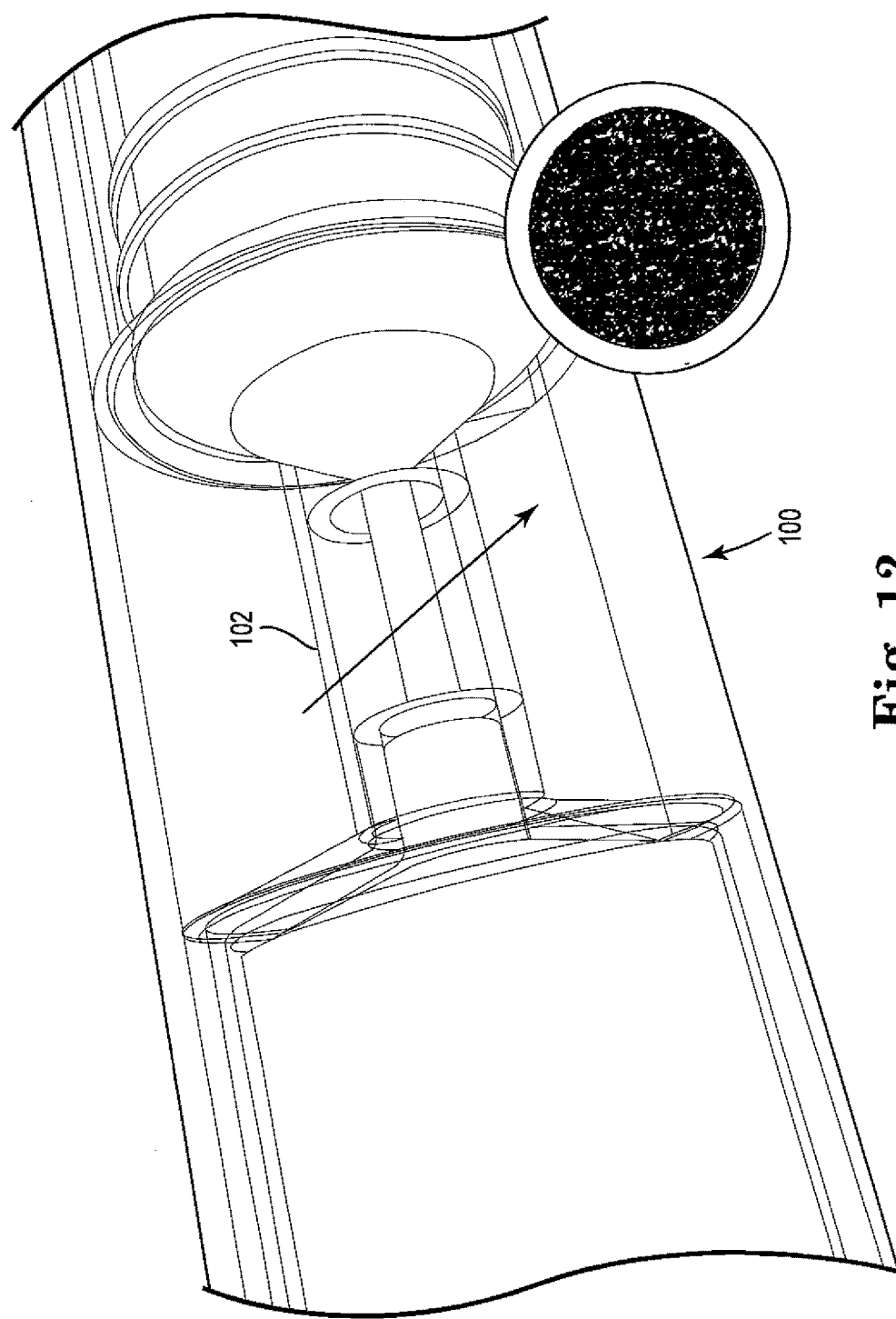
FIG. 12 is a perspective view of a portion of a fluid management system of the invention that includes nanofibers along the fluid path, and including an enlarged cross-sectional view of a portion of the system having nanofibers.

The fluid management systems of the invention may further be provided with filters in one or more locations along the fluid pathway and/or nanofibers that are designed to remove specific components from the fluid (e.g., certain types or sizes of particles). FIG. 12 illustrates an enlarged view of a portion of one embodiment of a fluid management system 100 that includes such nanofibers located along the fluid path, which are designed to pull components out of the fluid during the fluid transfer process. In particular, FIG. 12 also shows a cross-sectional view of a central channel 102 that includes nanofibers. This and other systems of the invention can include filtration features that are described above relative to FIGS. 5 and 6; however, in one particular exemplary embodiment, the fluid system includes a nanofiber network comprising a fiber diameter of about 30 nm to about 1200 nm, average interfiber spacing of about 100 nm to about 600 nm, and solidity of about 70 percent or less. The nanofibers can be fabricated from a variety of polymers or polymer systems, such as a polyamide or polyester, for example.

Figure 13:
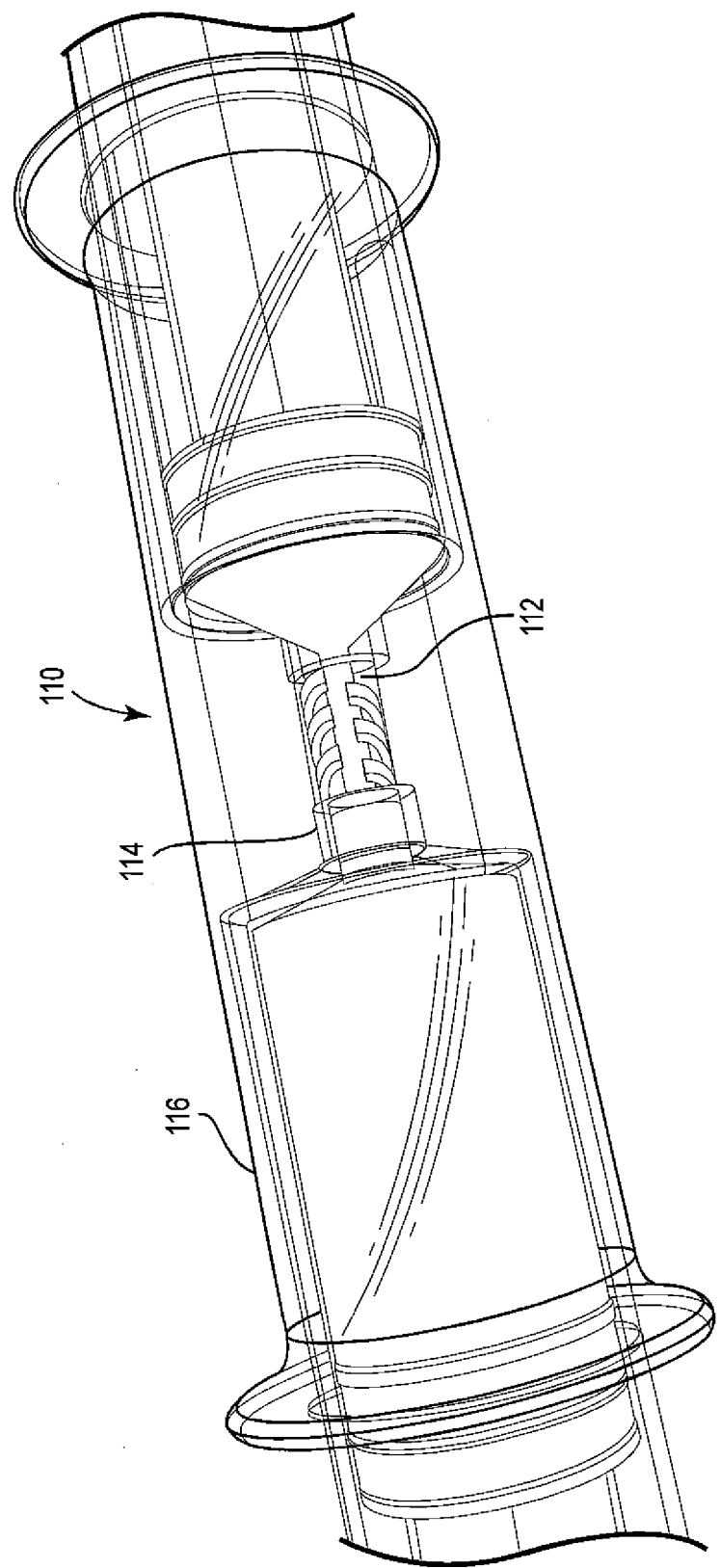
FIG. 13 is a perspective view of a portion of a fluid management system of the invention that includes multiple mixing elements in the fluid pathway.
Figure 14:
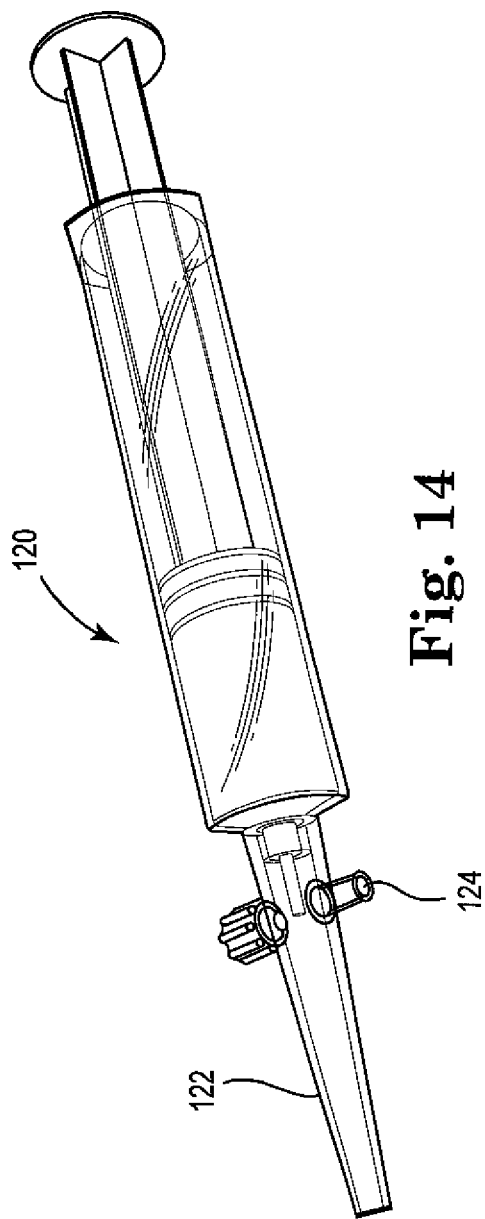
FIGS. 14 and 15 are perspective views of syringes having at least one Luer port that can be used with the methods and systems of the invention.

In order to mix or otherwise agitate the fluid during the fluid transfer process, ribs, nubs, or other extensions can be provided within a fluid pathway between the syringes of a fluid management system of the invention. One example of such a configuration is illustrated in a fluid management system 110 of FIG. 13, which includes a number of angled fingers or extensions 112 positioned generally in a channel 114 of a connector component 116 to promote mixing of the fluid or fluids as they move from one syringe to the other through the channel 114. The number, size, positioning, orientation, etc. of these extensions 112 can be different from that shown, and the extensions of any particular system can be specifically designed or selected to promote a desired amount of fluid mixing. The specific desired mixing forces necessary for particular components or materials will be a factor in determining the characteristics chosen or designed for the mixing elements.

Additional embodiments of syringes 120, 130, 140, and 150 that can be used with the fluid management systems of the invention are illustrated in FIGS. 14 through 17, respectively. These syringe embodiments each include a plunger that is insertable into a barrel at its proximal end. The syringe 150 of FIG. 17 includes a tapered tip portion 152, and the syringe 120 of FIG. 14 also includes a tapered tip portion 122, which includes a luer port 124 that provides a location to introduce fluids during the fluid transfer process. The tapered tip portions of these embodiments can cause the fluid to become activated or agitated due to the increased pressure placed on the fluid as is moved through the decreasing diameter of the tip toward its open end. In some cases, this activation of the fluid can eliminate a processing step that would need to otherwise be performed separately.

Figure 15:
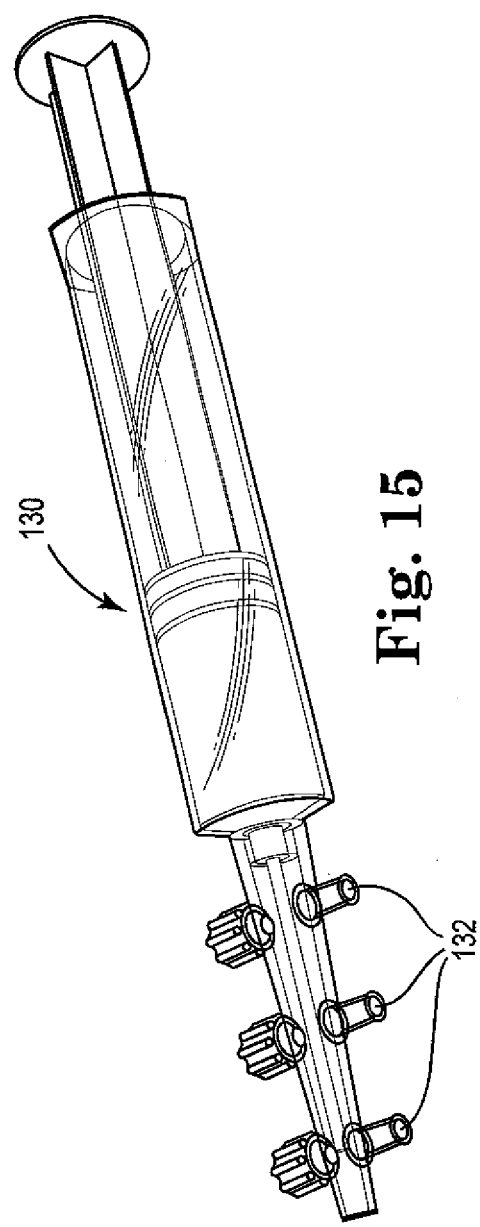
Figure 16:
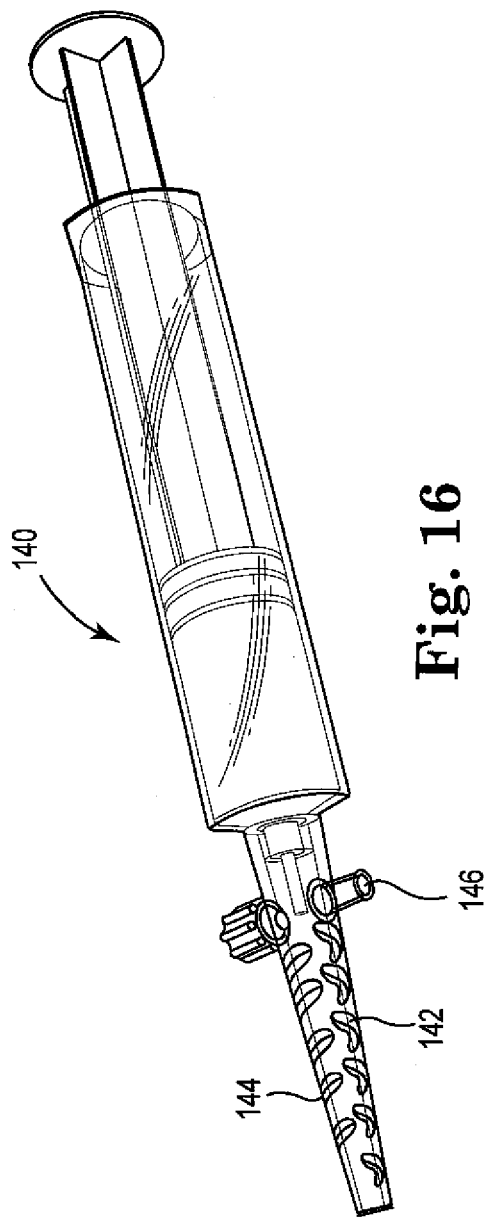
FIG. 16 is a perspective view of a syringe having a leer port and mixing elements that can be used with the methods and systems of the invention.
Figure 17:
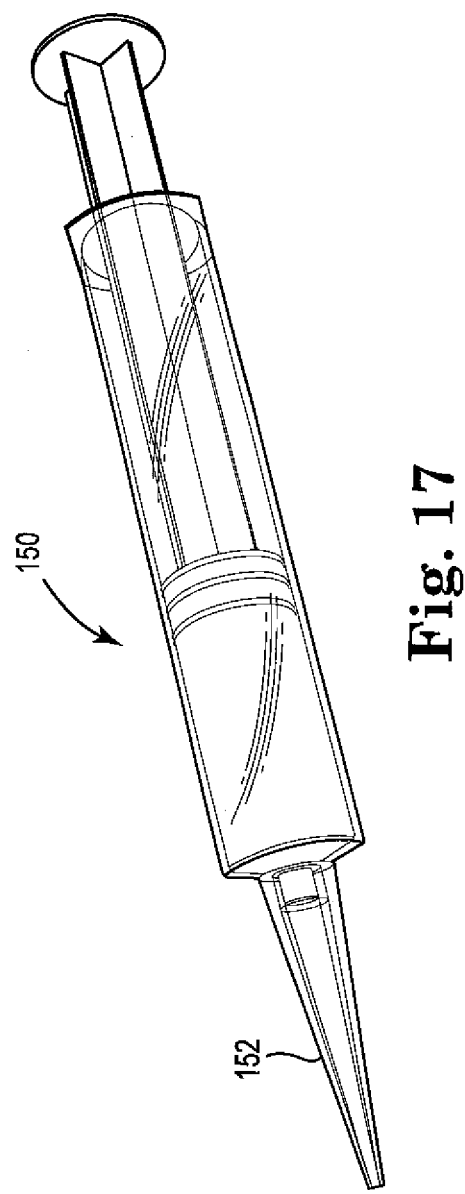
FIG. 17 is a perspective view of a syringe having a nozzle that can be used with the methods and systems of the invention.

FIG. 15 illustrates a syringe 130 that includes three separate luer ports 132 to allow for the addition of three separate components, if desired. FIG. 16 illustrates another syringe 140 that is similar to that of FIG. 14, although this syringe 140 also includes mixing nubs or extensions 142 within a tapered tip portion 144, along with at least one luer port 146 positioned along the tapered tip portion 144 of the syringe 140. Any of the fluid management systems of the invention may additionally or alternatively include luer ports that are provided in different and/or additional locations and/or quantities along one or more of the syringes and/or the connector component so that additional fluids or substances can be added to the sterile fluid during its transfer.

Figure 18:
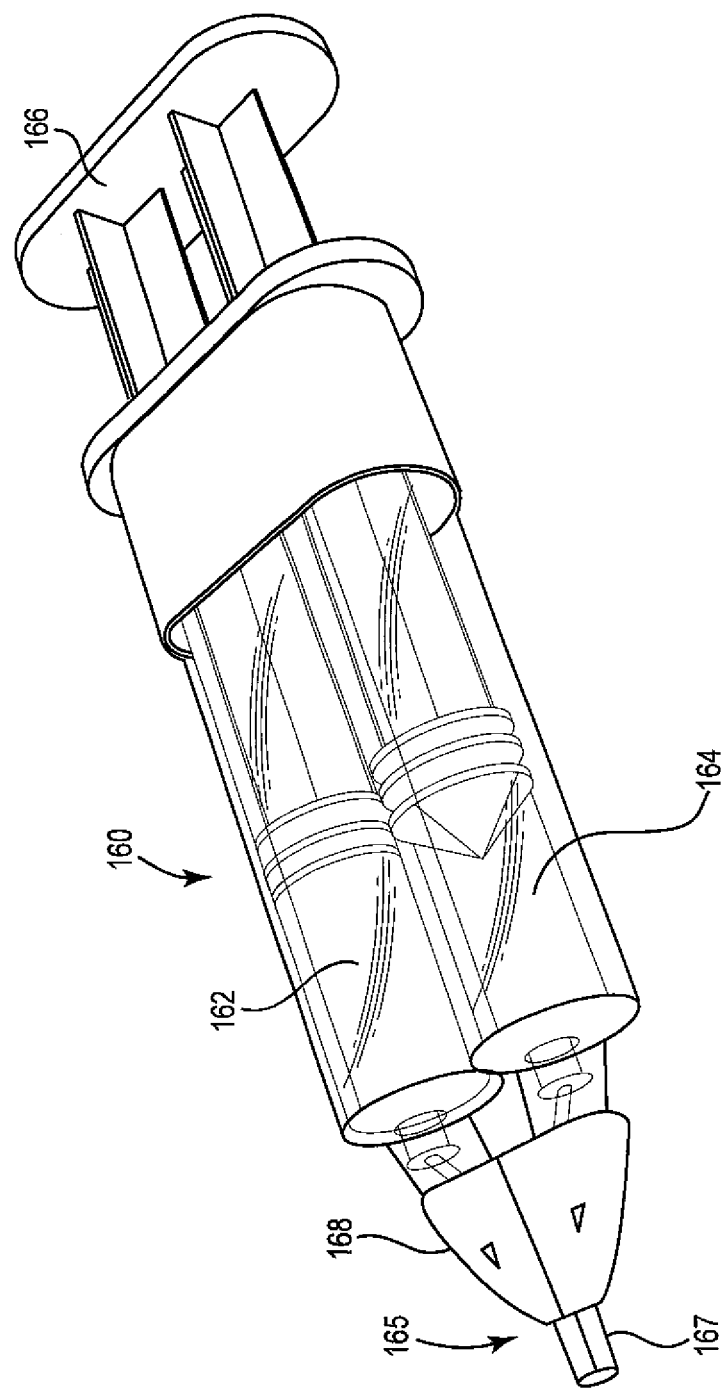
FIG. 18 is a perspective view of a multiple syringe adaptor or connector component for use with a fluid management system of the invention.

A syringe 160 that can introduce multiple fluids into a fluid management system in accordance with the invention is illustrated in FIG. 18. The syringe 160 is provided with two barrels 162, 164, and two fluids are shown as being provided in the barrels 162, 164. However, it is understood that additional barrels can be provided if it is desired to supply more than two fluids. In this embodiment, the syringe 160 includes two barrels 162, 164, a dual plunger 166 at its proximal end, and a mixing insert 168 at its distal end 165. To dispense fluid from the distal end 165 of the syringe 160, the plunger 166 is pushed toward the distal end 165, thereby forcing fluid from the barrels 162, 164 and into the mixing insert 168. After the fluid passes through the mixing insert 168, it can be dispensed from the syringe 160 through a syringe tip 167 and into a connector component, as described above relative to other embodiments of the invention. It is contemplated that additional mixing of the fluids can be caused or promoted within the connector component, such as when the connector component is provided with mixing extensions or fingers within the fluid path, as described above relative to FIG. 13, for example.

FIGS. 19 and 20 illustrate additional embodiments fluid management systems 170, 180, respectively, of the invention. Fluid management system 170 includes a dual syringe device 172 having two barrels, which supplies materials or fluids to a single receiver syringe 174 through a connector component 176. The connector component 176 includes multiple internal channels 178 that merge together to provide a single fluid supply to the receiver syringe 174. Similarly, fluid management system 180 includes a triple syringe device 182, which supplies materials or fluids to a single receiver syringe 184 through a connector component 186. The connector component 186 includes multiple internal channels 188 that merge together to provide a single fluid supply to the receiver syringe 184. However, it is understood that a connector component in accordance with the invention can have any number of ports or openings into which one or more syringes can be inserted for transfer of fluids. Each of the multiple syringe devices, such as devices 172, 182, can have plungers that are independently moveable within their respective barrels relative to other plungers, or the plungers of all of the syringes in a multiple barrel syringe can be linked or connected to each other so that they all move together.

Figure 21:
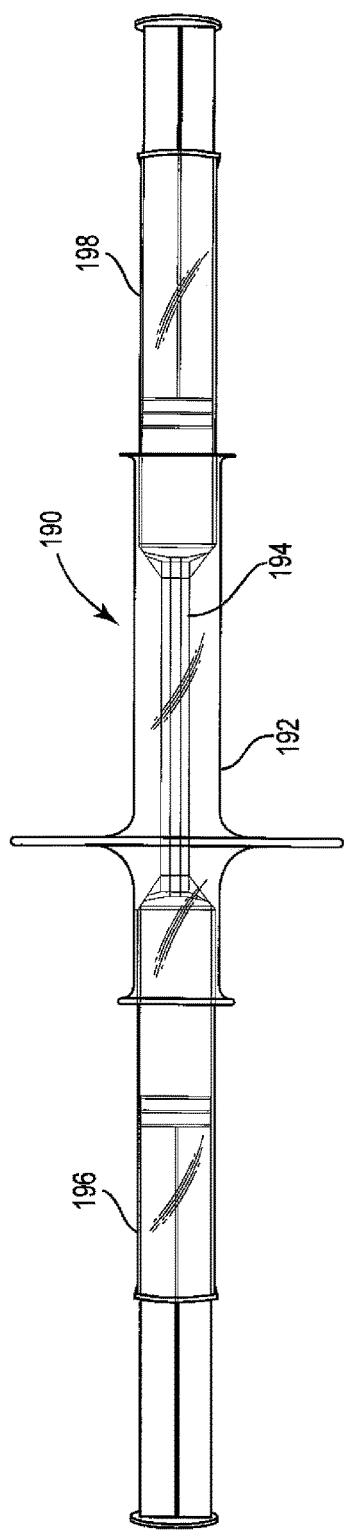
FIG. 21 is a side view of another fluid management system of the invention.

FIG. 21 illustrates a fluid management system 190 that includes a connector component 192 having a relatively long internal channel 194 through which fluid can travel between the syringes 196, 198. Such an extended channel length can provide additional locations to place filters and/or other materials through which the fluid can pass during fluid transfer.

Figure 22:
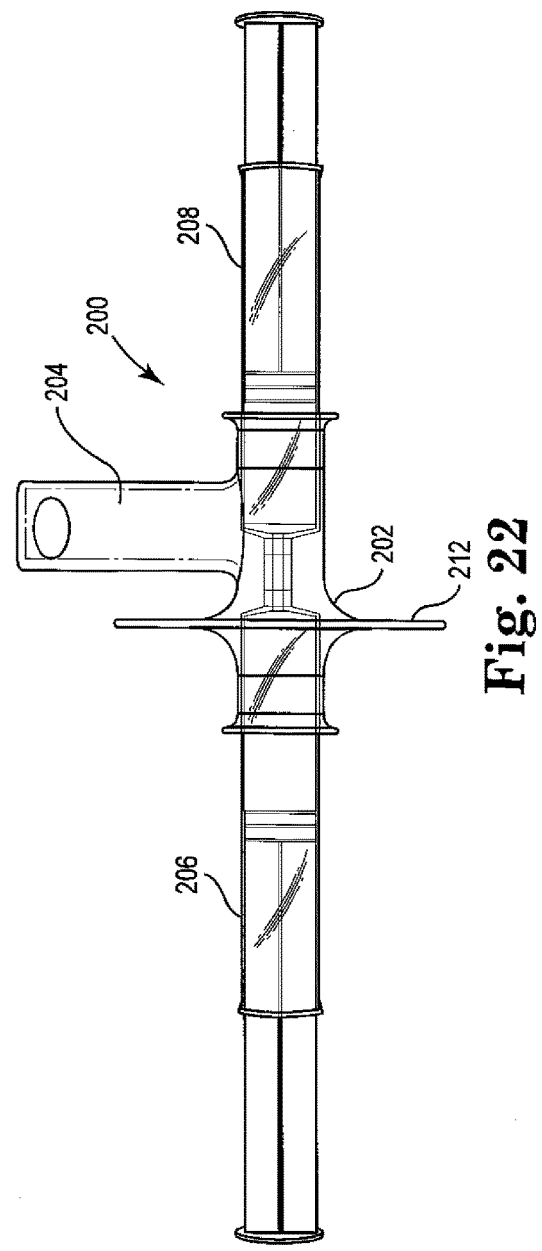
FIG. 22 is a side view of a fluid management system including a connector component having a stabilizer bar.

FIG. 22 illustrates a fluid management system 200 having a connector component 202 with a handle or extending portion 204. The system 200 further includes a first syringe 206 attached to one end of the connector component 202 and a second syringe 208 attached to the opposite end of the connector component 202. As with other embodiments of the invention described herein, fluid can be moved from one of the syringes to the other through the connector component 202. The extending portion 204 of the connector component 202 can provide an operator with additional stability for grasping the device during a fluid transfer process, for example. The extending portion 204 can have a different configuration than shown (e.g., it can be differently sized or shaped, can have additional gripping surfaces, and the like). It is further contemplated that the connector component 202 can comprise an extending portion on both sides of its boundary indicator 212.

FIGS. 23 and 24 are fluid management systems 230, 240 of the invention, respectively. The system 230 includes a connector component 232 with an extending portion 234 extending from its outer curved surface. The extending portion 234 includes a rotatable valve 235 that can be used to control the inflow of additional fluids to the connector component 232 and/or to a third channel 236 within the connector component 232. The connector component 232 includes a first end 231 and a second end 233. The first end 231 includes a first channel 237 and the second end 233 includes a second channel 238. The first channel 237 and the second channel 238 are connected to one another by the third channel 236. As shown in FIG. 23, the third channel 236 includes an internal diameter that is smaller than internal diameters of the first channel 237 and the second channel 238. Similarly, the system 240 includes a connector component 242 with an extending portion 244 extending from its outer curved surface. The extending portion 244 is considerably shorter than the extending portion 234 of system 230, but also includes a rotatable valve 245 that can be used to control the inflow of additional fluids to the connector component 242 and/or to a third channel 246 within the connector component 242. That is, these extending portions 234, 244 can optionally be in fluid communication with the fluid transfer channel of their respective connector components. The connector component 242 includes a first end 241 and a second end 243. The first end 241 includes a first channel 247 and the second end 243 includes a second channel 248. The first channel 247 and the second channel 248 are connected to one another by the third channel 246. As shown in FIG. 24, the third channel 246 includes an internal diameter that is smaller than internal diameters of the first channel 247 and the second channel 248.

FIGS. 25 and 26 illustrate sequential steps for using a fluid management system 250 of the invention in a fluid management process. Fluid management system 250 includes a fluid container 252 to which a connector component 254 can be permanently or removably attached. The system 250 further includes a syringe 256, which is shown in FIG. 25 as containing a volume of fluid 258 within its internal barrel. It is noted that the fluid container 252 includes an inner fluid reservoir 260 that does not contain any fluid in FIG. 25, but that is designed to accept fluid from a syringe. The connector component 254 is configured to accept the syringe 256 on one side and attach to the fluid container 252 on another side. The inner fluid reservoir 260 is shown in these Figures as being substantially smaller than the overall size of the fluid container 252; however, the inner reservoir 260 may instead be smaller or larger than shown. All or some of the fluid 258 can be transferred to the fluid reservoir 260 of the fluid container 252 by attaching the syringe 256 to the connector component 254 and pushing a barrel 262 of the syringe 256 toward its distal tip, thereby forcing fluid into the reservoir 260, as illustrated in FIG. 26. When a desired volume of fluid 258 has been transferred to the reservoir 260, the syringe 256 can be detached from the connector component 254. The connector component 254 can also be detached from the fluid container 252, if desired.

Figure 27:
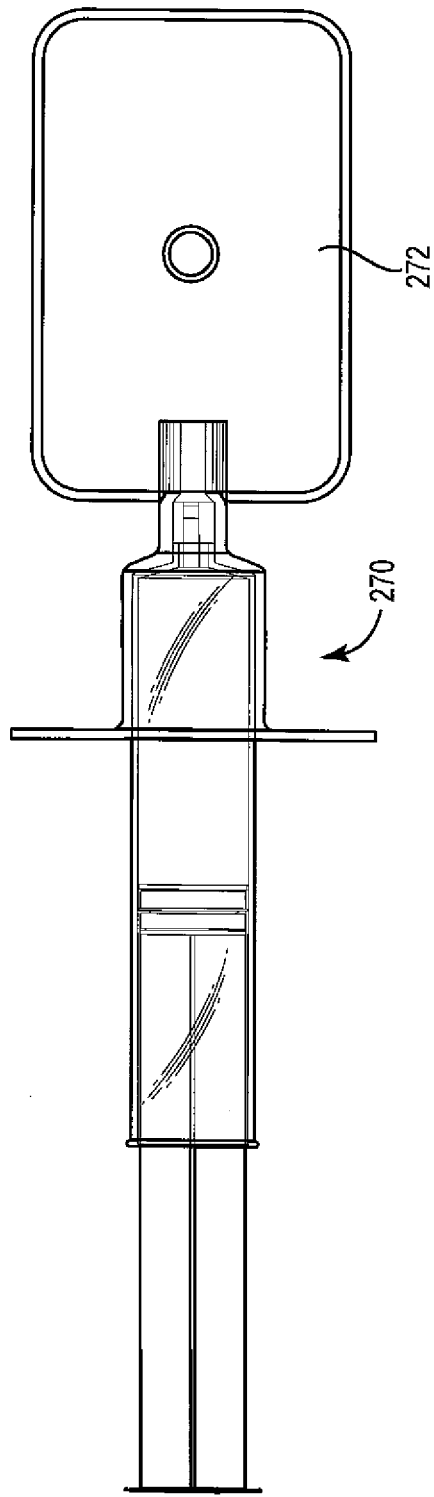
FIGS. 27 and 28 are side and perspective views, respectively, of a fluid management system of the invention.
Figure 28:
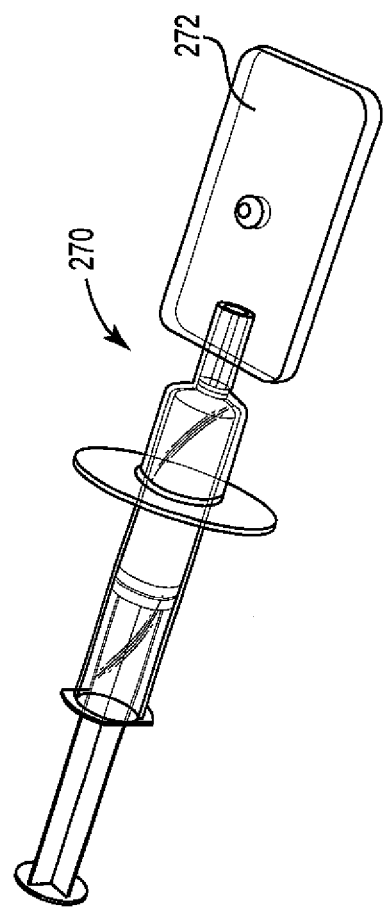

FIGS. 27 and 28 illustrate another embodiment of a fluid management system 270 that is similar to system 250 described relative to FIGS. 25 and 26. In this embodiment, a fluid container 272 is provided that generally comprises a shell with an internal area that can accept fluid transferred from a syringe. This fluid container 272 thus has a different configuration than the fluid container 252 described above, which may be desirable for certain applications, such as reconstituting, impregnating, infusing, or bathing a material, such as an allograft.

Figure 29:
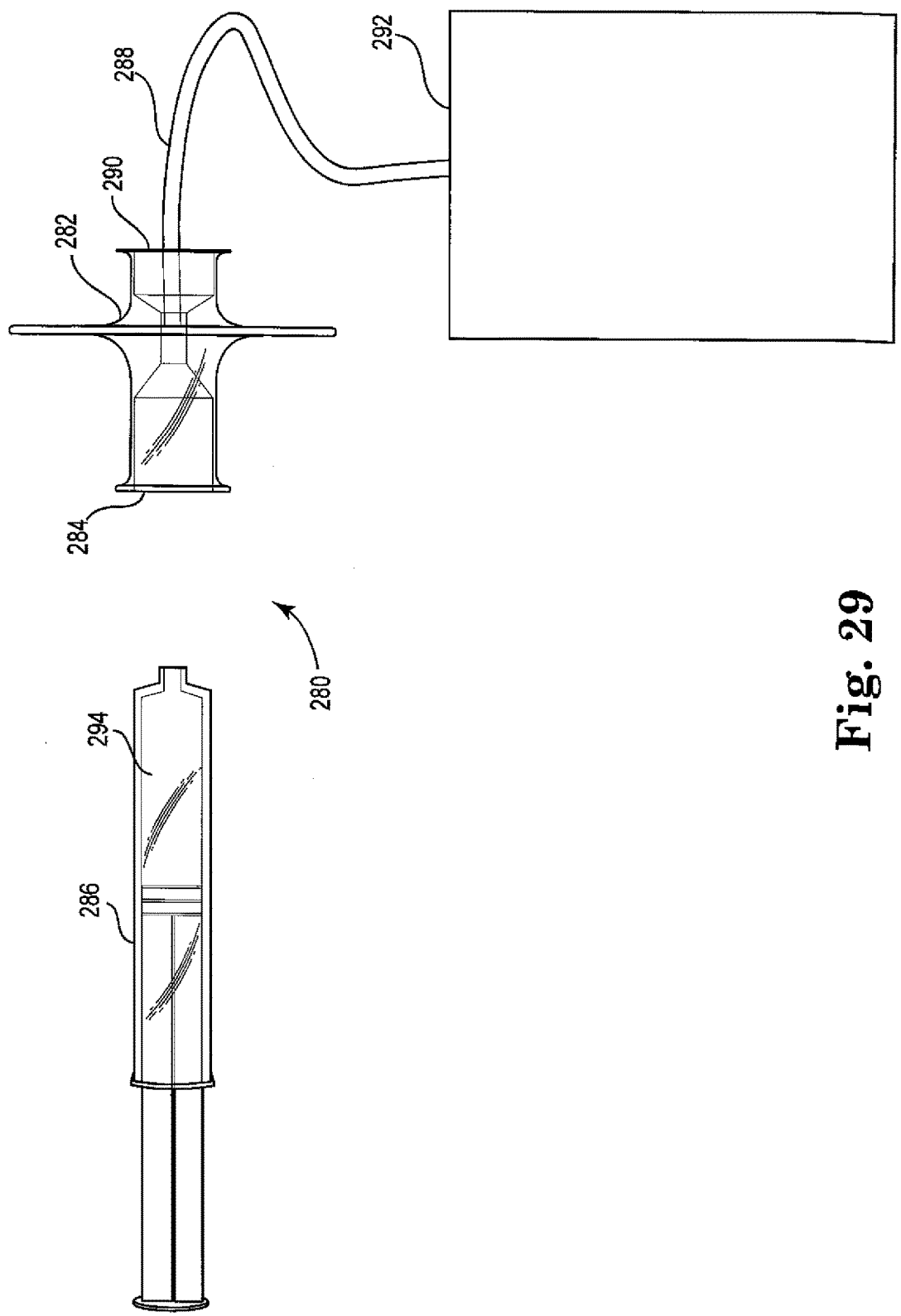
FIGS. 29 and 30 are side views of a fluid management system of the invention illustrating sequential steps in a fluid transfer process.
Figure 30:
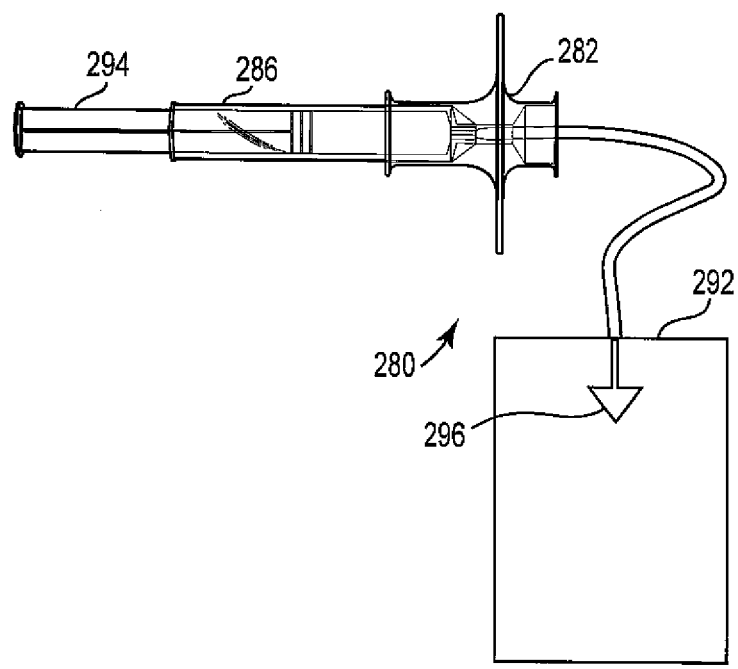
Figure 31:
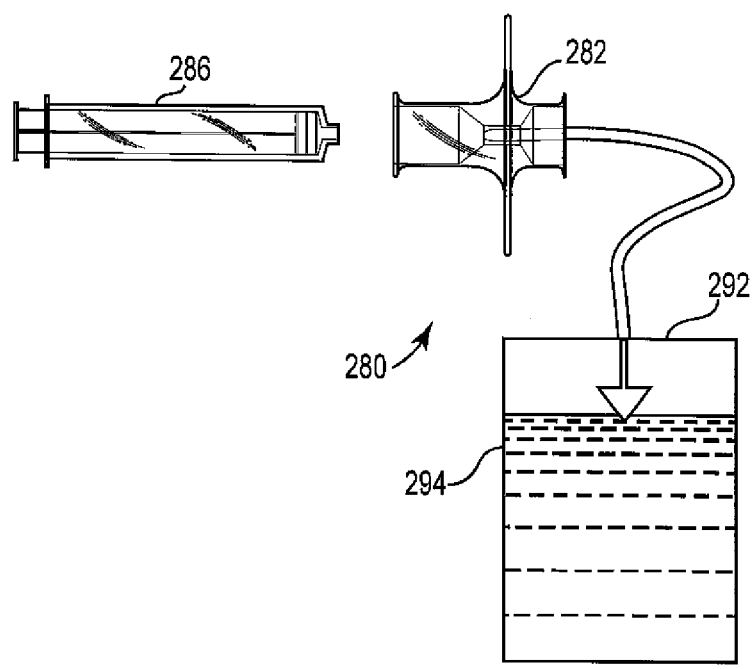
FIG. 31 is a side view of a fluid management system of FIGS. 29 and 30 at a fluid transfer step where fluid has been transferred through a connector component and tube to a fluid bag.

FIGS. 29-31 illustrate another embodiment of a fluid management system 280 of the invention, which includes a connector component 282 having an opening or receiver port 284 at one end into which a syringe 286 can be inserted, and a tube 288 extending from an opposite end 290 that is attachable to a bag 292 or other fluid-receiving container. The bag 292 can be flexible or rigid. The tube 288 can be relatively long or short, depending on the desired fluid transfer process. The tube 288 can be removable from the bag 292, if desired, such as through the use of a fitting that allows the bag 292 to be removed from the tube 288 without allowing fluid to leak from the bag. Further, the tube 288 can be permanently or removeably attached to the connector component.

With continued reference to the sequential steps of FIGS. 29-31, FIG. 29 illustrates the connector component 282 attached to the bag 292 via the tube 288, and the separate syringe 286, which includes fluid 294 within its barrel. The syringe 286 can then be attached to the connector component 282, as illustrated in FIG. 30, and fluid can begin to be transferred from the syringe 286 to the bag 292 by pressing a plunger 294 of the syringe 286 toward its distal end to move fluid in a direction indicated by arrow 296. After a desired amount of fluid is transferred from the syringe 286, it can be disconnected from the connector component 282, as is illustrated in FIG. 31. It is noted that FIG. 31 also illustrates the bag 292 with a volume of fluid 294 contained therein.

FIGS. 32a-32e illustrate sequential fluid transfer steps using another embodiment of a fluid management system 300 of the invention, which includes a syringe 302, a connector component 304, a tube 306, and a bag or reservoir 308. These components can all be removably attachable to each other, or some of the components may be permanently or semi-permanently connected to each other. For example, the tube 306 can be permanently attached to the connector component 304, as is illustrated in FIG. 32e. FIG. 32a shows the syringe 302 containing a volume of fluid, FIG. 32b shows the syringe 302 attached to the connector component 304 prior to fluid transfer, and FIG. 32c shows the syringe 302 as having no fluid within its barrel and with the fluid being contained within the bag 308. FIGS. 32d and 32e illustrate the components of the system 300 detached from each other after the fluid transfer process is completed. It is noted that the bag 308 can include a self-closing seal 309 or other sealing configuration that prevents fluid from leaking from the bag 308 after it has been transferred to it from the syringe 302.

FIGS. 33a-33e illustrate sequential fluid transfer steps using another embodiment of a fluid management system 310 of the invention. System 310 includes a syringe 312, a connector component 314, a tube 316, and a bag or reservoir 318. This system is similar to that described above relative to FIGS. 32a-32e; however, in this embodiment, the tube 316 remains attached to the connector component 314, which in turn remains attached to the syringe 312 after these components are detached from the bag or reservoir 318.

Figure 34B:
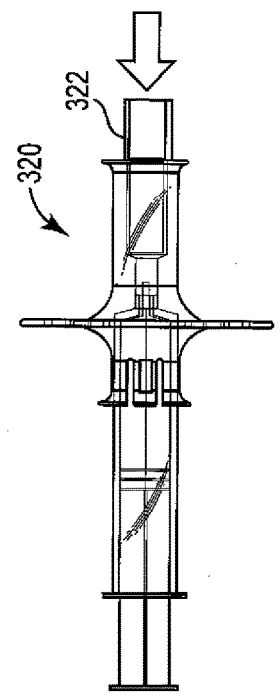
FIGS. 34a-34d are side views of a fluid management system of the invention illustrating sequential steps in a fluid transfer process for transferring fluid from a syringe to a vial or container.
Figure 34A:
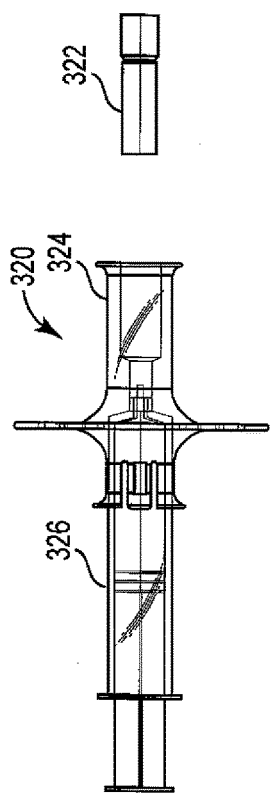
Figure 34D:
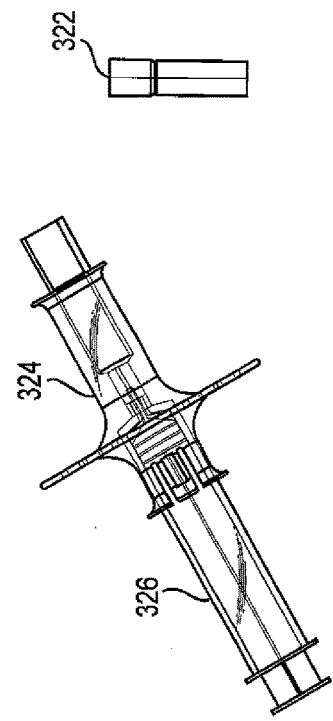
Figure 34C:
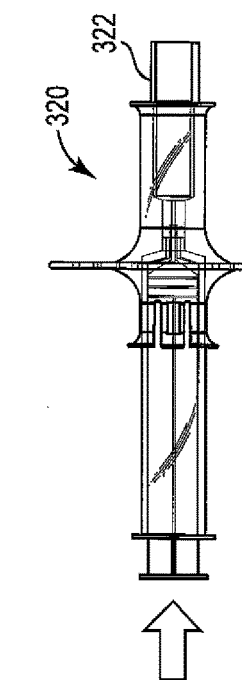

FIGS. 34a-34d illustrate sequential steps in fluid transfer processes using another embodiment of a fluid management system 320 of the invention. System 320 includes a vial or container 322, such as a container commercially available under the tradename "Vacutainer", to which fluid is transferred through a connector component 324 from a syringe 326. FIG. 34a illustrates the syringe 326 containing fluid and attached to the connector component 324 prior to the vial or container 322 being attached to the system. Once the container 322 is attached to the connector component 324 and fluid has been transferred from the syringe 326 into the container 322, as illustrated in FIG. 34b, the container 322 can be disconnected from the system, as illustrated in FIG. 34d. As shown in the Figures, once the fluid has been transferred from the syringe 326, the entire assembly can be moved from one field into the other, if desired.

Figure 35A:
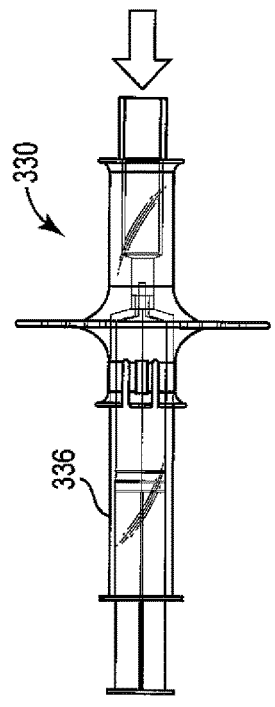
FIGS. 35a-35d are side views of a fluid management system of the invention illustrating sequential steps in a fluid transfer process for transferring fluid from a syringe to a vial or container.
Figure 35B:
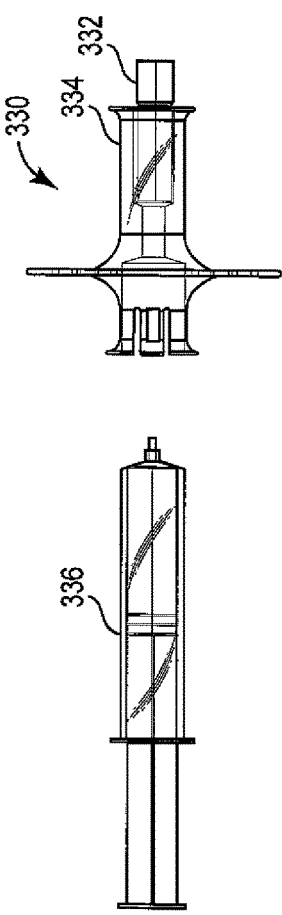
Figure 35D:
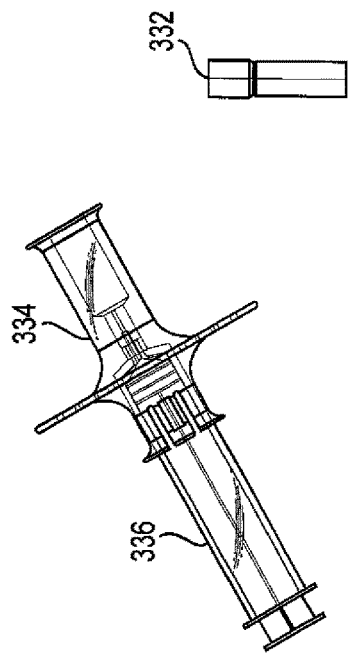
Figure 35C:
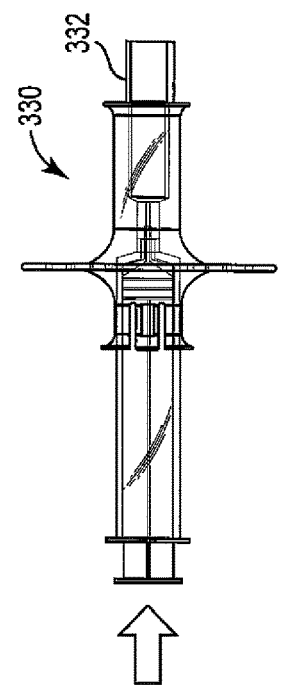
Figure 39A:
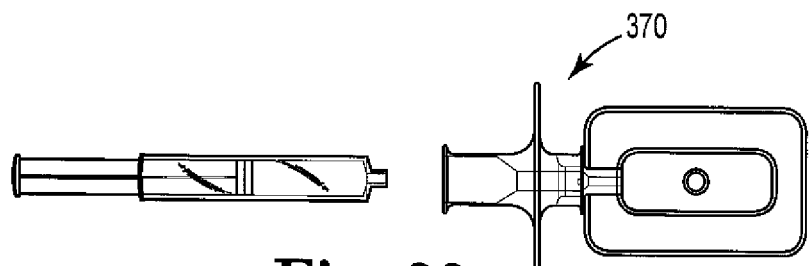
FIGS. 39a-39e are side views of fluid management systems of the invention illustrating sequential steps in fluid transfer processes including a fluid-receiving container.
Figure 39B:
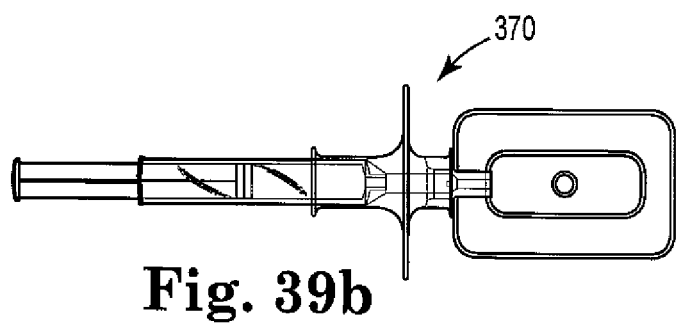
Figure 39C:
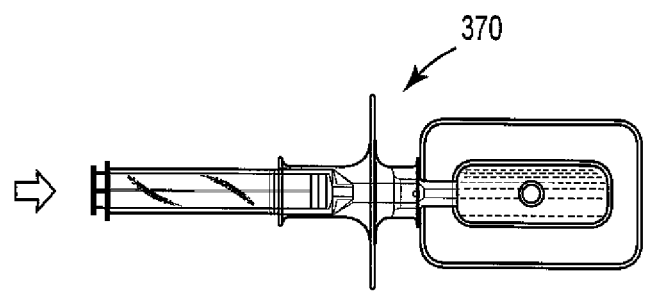
Figure 39D:
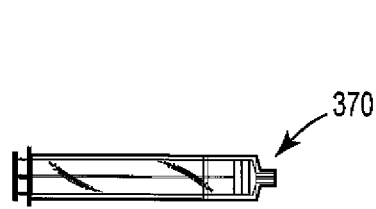
Figure 39E:
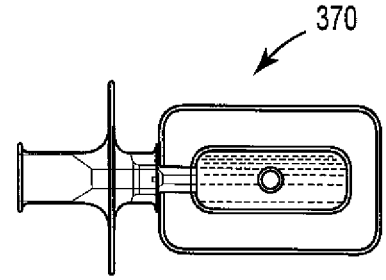
Figure 40A:
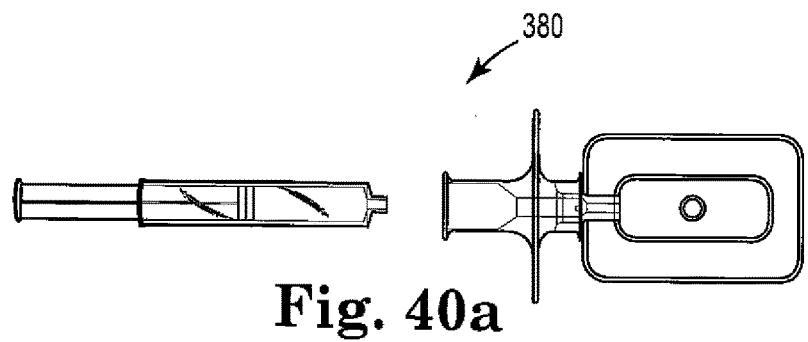
FIGS. 40a-40d are side views of fluid management systems of the invention illustrating sequential steps in fluid transfer processes including a fluid-receiving container.
Figure 40B:
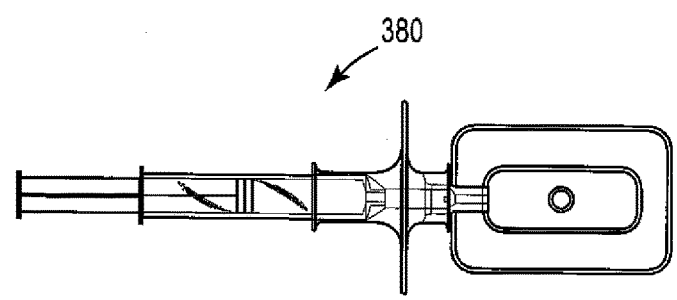
Figure 40C:
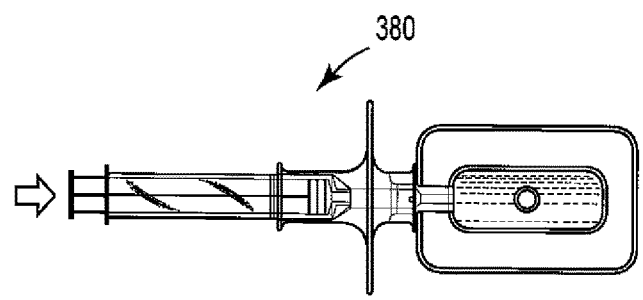
Figure 40D:
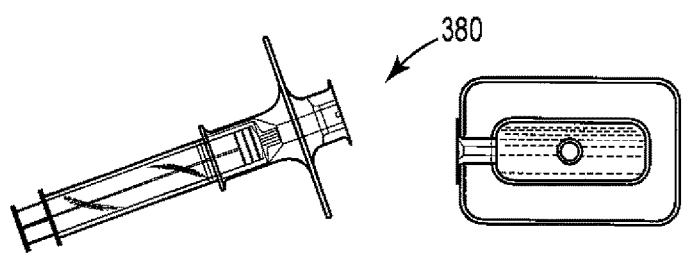

FIGS. 35a-35d illustrate a system 330 that is similar to the system 320; however, a vial or container 332 is attached to a connector component 334 prior to attachment of the connector component 334 to a syringe 336 containing fluid, as is illustrated in FIG. 35a. Again, once the syringe 336 is attached to the connector component 334 and fluid has been transferred from the syringe 336 into the container 332, as illustrated in FIG. 35c, the container 332 can be disconnected from the system, as is illustrated in FIG. 35d.

FIG. 36 and FIGS. 37a-37c are multiple views of a fluid management system 350 having a mechanism 356 on a connector component 352 that provides for positive engagement between a first syringe 354 and one side of the connector component 352. The mechanism 356 includes at least one moveable tab 358 for engagement with a syringe. Mechanism 356 may be configured so that the syringe 354 is not detachable from the connector component 352 once the syringe 354 is engaged with the mechanism (i.e., the mechanism acts as a lock between the components). Alternatively, the syringe can be removeable from the connector component after it has been attached thereto. The mechanism may further be configured so it engages with only specific types of syringes, thereby preventing unintentional attachment of certain syringes to a designated side of the connector component, for example. Features of this mechanism can be utilized with various embodiments of the present invention where it is determined that particular locking or engagement features are desirable.

FIGS. 38a-38c, FIGS. 39a-39e, and FIGS. 40a-40d illustrate sequential steps of fluid transfer processes using fluid management systems 360, 370, and 380, respectively. Each of these fluid management systems includes a fluid-receiving container. As shown, the various components of each of these systems can be attached and/or detached from each other before and/or after the transfer of fluid from a syringe to a fluid-receiving container.

As was briefly described above, the descriptions herein of fluid being transferred from a syringe to particular containers or syringes through a connector component can also be performed in an opposite direction in the embodiments of the invention. That is, fluid can also be transferred from a bag, box, or fluid-receiving container into a syringe, such as by retracting a plunger from a syringe to withdraw fluid from such a vessel or container.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A fluid management system for transferring fluid, the system comprising:
    a connector component comprising:
        an outer surface extending from a first end to a second end;
        a first channel extending from the first end towards the second end and having a first internal diameter;
        a second channel extending from the second end towards the first end and having a second internal diameter;
        a third channel fluidly connecting the first channel and the second channel, wherein a central axis of the third channel is axially aligned with a central axis of the connector component and the third channel comprises a third internal diameter that is smaller than the first and second internal diameters; and
    a sterile field boundary indicator extending outwardly from at least a portion of the outer surface of the connector component between its first and second ends, wherein the sterile field boundary indicator is a slotted disc, and wherein the sterile field boundary indicator is disposed on the connector component so as to be located between the first end and the second end of the connector component to indicate a location of a sterile field boundary.

2. The fluid management system of claim 1, further comprising at least one valve coupled to the third channel by an extending portion, the extending portion extending radially from the outer surface of the connector component into the third channel for fluid communication with the third channel, the at least one valve adapted to control inflow of fluids into the third channel.

3. The fluid management system of claim 2, wherein the third channel is pressurizable by the at least one valve.

4. The fluid management system of claim 1, further comprising:
 a first syringe that is slideably engageable within the first internal diameter of the connector component; and
 a second syringe slideably engageable within the second internal diameter of the connector component.

5. The fluid management system of claim 1, wherein the sterile field boundary indicator extends from the outer surface of the connector component around an entire perimeter of the connector component.

6. The fluid management system of claim 4, wherein a fluid is disposed in at least one of the first syringe, the second syringe, or the connector component, and wherein the fluid comprises at least one of a solution, a suspension, a cellular fluid, and a protein solution.

7. The fluid management system of claim 1, further comprising a handle extending radially from the outer surface of the connector component.

8. The fluid management system of claim 1, wherein the sterile field boundary indicator comprises a curved shield.

9. The fluid management system of claim 1, further comprising a plurality of mixing nubs disposed on an interior surface of the third channel and extending into the third channel so that the plurality of mixing nubs contact a fluid within the third channel.

10. The fluid management system of claim 2, wherein the at least one valve comprises a metering valve.

11. The fluid management system of claim 1, further comprising a moveable tab disposed at the first end of the connector component and adapted for engagement with a first syringe.

12. The fluid management system of claim 1, further comprising:
 a ring disposed at the first end of the connector component; and
 wherein the ring and the sterile field boundary indicator each comprise a matching visual marker to provide visual assurance of a proper placement of components of the fluid management system.

13. The fluid management system of claim 1, further comprising a plurality of nanofibers disposed within at least one of the first channel, the second channel, and the third channel.

14. The fluid management system of claim 1, further comprising a handle that extends from the connector component and provides additional stability for an operator of the fluid management system.

* * * * *